(12) United States Patent
Olson et al.

(10) Patent No.: US 10,575,869 B2
(45) Date of Patent: Mar. 3, 2020

(54) ENDOVASCULAR DEVICE WITH A TISSUE PIERCING DISTAL PROBE AND ASSOCIATED METHODS

(71) Applicant: BridgePoint Medical, Inc., Plymouth, MN (US)

(72) Inventors: Matthew J. Olson, Crystal, MN (US); Chad J. Kugler, Buffalo, MN (US); Ross A. Olson, Anoka, MN (US); David B. Robinson, Chanhassen, MN (US); Peter A. Jacobs, Minneapolis, MN (US)

(73) Assignee: BRIDGEPOINT MEDICAL, INC., Plymouth, MN (US)

( * ) Notice: Subject to any disclaimer, the term of this patent is extended or adjusted under 35 U.S.C. 154(b) by 1320 days.

(21) Appl. No.: 13/719,687

(22) Filed: Dec. 19, 2012

(65) Prior Publication Data

US 2013/0110144 A1  May 2, 2013

Related U.S. Application Data

(63) Continuation of application No. 12/461,261, filed on Aug. 5, 2009, now Pat. No. 8,337,425, which is a
(Continued)

(51) Int. Cl.
*A61B 17/3207* (2006.01)
*A61B 17/34* (2006.01)
(Continued)

(52) U.S. Cl.
CPC .......... *A61B 17/3207* (2013.01); *A61B 17/11* (2013.01); *A61B 17/3478* (2013.01); *A61M 25/09* (2013.01); *A61B 17/320758* (2013.01); *A61B 90/39* (2016.02); *A61B 2017/00252* (2013.01); *A61B 2017/00336* (2013.01); *A61B 2017/00438* (2013.01); *A61B 2017/00778* (2013.01); *A61B 2017/1107* (2013.01);
(Continued)

(58) Field of Classification Search
CPC ........ A61M 25/09; A61M 2025/09175; A61M 2025/09083
USPC ....................................................... 600/585
See application file for complete search history.

(56) References Cited

U.S. PATENT DOCUMENTS 3,749,086 A   7/1973   Kline
4,020,829 A   5/1977   Willson et al.
(Continued)

FOREIGN PATENT DOCUMENTS

CA   2209637 A1   7/1996
CA   2251685 A1   9/1998
(Continued)

*Primary Examiner* — Daniel L Cerioni
(74) *Attorney, Agent, or Firm* — Seager, Tufte & Wickhem LLP

(57) ABSTRACT

Devices, systems and methods for treating diseases and disorders effecting the cardiovascular system of the human body are disclosed. An exemplary device in accordance with this disclosure comprises a shaft, tip member fixed to the shaft, and a probe extending beyond a distal surface of the tip member. In some useful embodiments, the tip member is relatively atraumatic and the probe is shaped so as to be more likely to produce trauma than the tip member.

20 Claims, 27 Drawing Sheets

Related U.S. Application Data continuation-in-part of application No. 12/320,792, filed on Feb. 4, 2009, now Pat. No. 8,202,246.

(60) Provisional application No. 61/063,756, filed on Feb. 5, 2008, provisional application No. 61/104,868, filed on Oct. 13, 2008.

(51) Int. Cl.

| | | |
|---|---|---|
| *A61B 17/11* | (2006.01) | |
| *A61M 25/09* | (2006.01) | |
| A61B 90/00 | (2016.01) | |
| A61B 17/22 | (2006.01) | |
| A61B 17/00 | (2006.01) | |
| A61B 17/32 | (2006.01) | |
| A61M 25/00 | (2006.01) | |
| A61M 25/10 | (2013.01) | |

(52) U.S. Cl.
CPC ............ *A61B 2017/22044* (2013.01); *A61B 2017/22048* (2013.01); *A61B 2017/22054* (2013.01); *A61B 2017/22094* (2013.01); *A61B 2017/22095* (2013.01); *A61B 2017/320044* (2013.01); *A61B 2017/3488* (2013.01); *A61B 2090/036* (2016.02); *A61M 25/007* (2013.01); *A61M 25/1002* (2013.01); *A61M 25/1011* (2013.01); *A61M 2025/0096* (2013.01); *A61M 2025/09083* (2013.01); *A61M 2025/09183* (2013.01)

(56) References Cited

U.S. PATENT DOCUMENTS

| | | |
|---|---|---|
| 4,080,706 A | 3/1978 | Heilman et al. |
| 4,233,983 A | 11/1980 | Rocco |
| 4,534,363 A | 8/1985 | Gold et al. |
| 4,545,390 A | 10/1985 | Leary |
| 4,569,347 A | 2/1986 | Frisbie |
| 4,581,017 A | 4/1986 | Sahota |
| 4,619,274 A | 10/1986 | Morrison |
| 4,621,636 A | 11/1986 | Fogarty |
| 4,676,249 A | 6/1987 | Arenas et al. |
| 4,721,117 A | 1/1988 | Mar et al. |
| 4,747,821 A | 5/1988 | Kensey et al. |
| 4,748,986 A | 6/1988 | Morrison et al. |
| 4,762,130 A | 8/1988 | Fogarty et al. |
| 4,763,647 A | 8/1988 | Gambale |
| 4,774,949 A | 10/1988 | Fogarty et al. |
| 4,819,634 A | 4/1989 | Shiber et al. |
| 4,832,047 A | 5/1989 | Sepetka et al. |
| 4,841,976 A | 6/1989 | Packard et al. |
| 4,878,495 A | 11/1989 | Grayzel |
| 4,925,445 A | 5/1990 | Sakamoto et al. |
| 4,932,419 A | 6/1990 | De Toledo et al. |
| 4,976,689 A | 12/1990 | Buchbinder et al. |
| 4,979,939 A | 12/1990 | Shiber et al. |
| 4,984,581 A | 1/1991 | Stice |
| 4,990,134 A | 2/1991 | Auth |
| 4,991,602 A | 2/1991 | Amplatz et al. |
| 5,052,404 A | 10/1991 | Hodgson et al. |
| 5,067,489 A | 11/1991 | Lind |
| 5,069,226 A | 12/1991 | Yamauchi et al. |
| 5,071,406 A | 12/1991 | Jang et al. |
| 5,118,907 A | 6/1992 | Stout |
| 5,120,308 A | 6/1992 | Hess et al. |
| 5,127,917 A | 7/1992 | Niederhauser et al. |
| 5,129,890 A | 7/1992 | Bates et al. |
| 5,143,122 A | 9/1992 | Adkins et al. |
| 5,147,317 A | 9/1992 | Shank et al. |
| 5,154,705 A | 10/1992 | Fleischhacker et al. |
| 5,171,383 A | 12/1992 | Sagae et al. |
| 5,174,302 A | 12/1992 | Palmer et al. |
| 5,193,546 A | 3/1993 | Shaknovich |
| 5,201,753 A | 4/1993 | Lampropoulos et al. |
| 5,213,111 A | 5/1993 | Cook et al. |
| 5,228,453 A | 7/1993 | Sepetka |
| 5,230,348 A | 7/1993 | Ishibe et al. |
| 5,238,004 A | 8/1993 | Sahatjian et al. |
| 5,242,759 A | 9/1993 | Hall |
| 5,243,996 A | 9/1993 | Hall |
| 5,259,393 A | 11/1993 | Corso et al. |
| 5,263,493 A | 11/1993 | Avitall |
| 5,275,610 A | 1/1994 | Eberbach et al. |
| 5,282,478 A | 2/1994 | Fleischhaker, Jr. et al. |
| 5,303,714 A | 4/1994 | Abele et al. |
| 5,324,263 A | 6/1994 | Kraus et al. |
| 5,333,620 A | 8/1994 | Moutafis et al. |
| 5,354,257 A | 10/1994 | Roubin et al. |
| 5,354,623 A | 10/1994 | Hall et al. |
| 5,356,418 A | 10/1994 | Shturman |
| 5,363,847 A | 11/1994 | Viera |
| 5,365,942 A | 11/1994 | Shank et al. |
| 5,368,048 A | 11/1994 | Stoy et al. |
| 5,368,049 A | 11/1994 | Raman et al. |
| 5,372,144 A | 12/1994 | Mortier et al. |
| 5,372,587 A | 12/1994 | Hammerslag et al. |
| 5,373,856 A | 12/1994 | Grenouillet |
| 5,379,779 A | 1/1995 | Rowland et al. |
| 5,383,856 A | 1/1995 | Bersin et al. |
| 5,385,152 A | 1/1995 | Abele et al. |
| 5,409,453 A | 4/1995 | Lundquist et al. |
| 5,415,178 A | 5/1995 | Hsi et al. |
| 5,415,637 A | 5/1995 | Khosravi et al. |
| 5,421,349 A | 6/1995 | Rodriguez et al. |
| 5,443,907 A | 8/1995 | Slaikeu et al. |
| 5,458,585 A | 10/1995 | Salmon et al. |
| 5,464,395 A | 11/1995 | Faxon et al. |
| 5,465,733 A | 11/1995 | Hinohara et al. |
| 5,477,864 A | 12/1995 | Davidson et al. |
| 5,488,959 A | 2/1996 | Ales |
| 5,498,250 A | 3/1996 | Prather |
| 5,501,667 A | 3/1996 | Verduin |
| 5,505,702 A | 4/1996 | Arney et al. |
| 5,531,781 A | 7/1996 | Alferness et al. |
| 5,534,007 A | 7/1996 | St. Germain et al. |
| 5,542,434 A | 8/1996 | Imran et al. |
| 5,555,883 A | 9/1996 | Avitall |
| 5,571,122 A | 11/1996 | Kelly et al. |
| 5,571,169 A | 11/1996 | Plaia et al. |
| 5,603,720 A | 2/1997 | Kieturakis et al. |
| 5,622,184 A | 4/1997 | Ashby et al. |
| 5,636,641 A | 6/1997 | Fariabi et al. |
| 5,637,089 A | 6/1997 | Abrams et al. |
| 5,640,970 A | 6/1997 | Arenas |
| 5,643,298 A | 7/1997 | Nordgren et al. |
| 5,645,529 A | 7/1997 | Fagan et al. |
| 5,655,548 A | 8/1997 | Nelson et al. |
| 5,664,580 A | 9/1997 | Erickson et al. |
| 5,695,111 A | 12/1997 | Nanis et al. |
| 5,695,506 A | 12/1997 | Pike et al. |
| 5,720,300 A | 2/1998 | Fagan |
| 5,722,424 A | 3/1998 | Engelson |
| 5,728,133 A | 3/1998 | Kontos et al. |
| 5,741,270 A | 4/1998 | Hansen et al. |
| 5,741,429 A | 4/1998 | Donadio et al. |
| 5,769,796 A | 6/1998 | Palermo et al. |
| 5,779,721 A | 7/1998 | Nash et al. |
| 5,807,241 A | 9/1998 | Heimberger et al. |
| 5,824,071 A | 10/1998 | Nelson et al. |
| 5,830,222 A | 11/1998 | Makower et al. |
| 5,830,224 A | 11/1998 | Cohn et al. |
| 5,833,631 A | 11/1998 | Nguyen |
| 5,840,046 A | 11/1998 | Deem |
| 5,843,050 A | 12/1998 | Jones et al. |
| 5,871,528 A | 2/1999 | Camps et al. |
| 5,882,329 A | 3/1999 | Patterson et al. |
| 5,885,227 A | 3/1999 | Finlayson |
| 5,891,055 A | 4/1999 | Sauter |
| 5,910,133 A | 6/1999 | Gould et al. |
| 5,916,194 A | 6/1999 | Jacobsen et al. |
| 5,924,998 A | 7/1999 | Cornelius et al. |
| 5,935,108 A | 8/1999 | Katoh et al. |

(56) References Cited

U.S. PATENT DOCUMENTS

| | | |
|---|---|---|
| 5,944,686 A | 8/1999 | Patterson et al. |
| 5,947,940 A | 9/1999 | Beisel et al. |
| 5,951,494 A | 9/1999 | Wang et al. |
| 5,954,713 A | 9/1999 | Newman et al. |
| 5,957,900 A | 9/1999 | Ouchi et al. |
| 5,968,064 A | 10/1999 | Selmon et al. |
| 5,984,878 A | 11/1999 | Engelson |
| 5,989,276 A | 11/1999 | Houser et al. |
| 5,997,517 A | 12/1999 | Whitbourne |
| 6,010,449 A | 1/2000 | Selmon et al. |
| 6,013,055 A | 1/2000 | Bampos et al. |
| 6,015,405 A | 1/2000 | Schwartz et al. |
| 6,022,343 A | 2/2000 | Johnson et al. |
| 6,027,460 A | 2/2000 | Shturman |
| 6,036,707 A | 3/2000 | Spaulding et al. |
| 6,036,717 A | 3/2000 | Mers Kelly et al. |
| 6,042,876 A | 3/2000 | Deem |
| 6,059,750 A | 5/2000 | Fogarty et al. |
| 6,068,638 A | 5/2000 | Makower et al. |
| 6,071,281 A | 6/2000 | Burnside et al. |
| 6,071,292 A | 6/2000 | Makower et al. |
| 6,081,738 A | 6/2000 | Hinohara et al. |
| 6,099,542 A | 8/2000 | Cohn et al. |
| 6,106,485 A | 8/2000 | McMahon |
| 6,117,064 A | 9/2000 | Apple et al. |
| 6,120,516 A | 9/2000 | Selmon et al. |
| 6,126,649 A | 10/2000 | VanTassel et al. |
| 6,139,540 A | 10/2000 | Rost et al. |
| 6,155,264 A | 12/2000 | Ressemann et al. |
| 6,157,852 A | 12/2000 | Selmon et al. |
| 6,159,225 A | 12/2000 | Makower et al. |
| 6,183,432 B1 | 2/2001 | Milo |
| 6,186,972 B1 | 2/2001 | Nelson et al. |
| 6,190,353 B1 | 2/2001 | Makower et al. |
| 6,203,559 B1 | 3/2001 | Davis |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,245,030 B1 | 6/2001 | DuBois et al. |
| 6,246,914 B1 | 6/2001 | de la Rama et al. |
| 6,254,588 B1 | 7/2001 | Jones et al. |
| 6,258,052 B1 | 7/2001 | Milo |
| 6,266,550 B1 | 7/2001 | Selmon et al. |
| 6,277,133 B1 | 8/2001 | Kanesaka |
| 6,283,940 B1 | 9/2001 | Mulholland |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,337,142 B2 | 1/2002 | Harder et al. |
| 6,358,244 B1 | 3/2002 | Newman et al. |
| 6,375,615 B1 | 4/2002 | Flaherty et al. |
| 6,387,119 B2 | 5/2002 | Wolf et al. |
| 6,398,798 B2 | 6/2002 | Selmon et al. |
| 6,416,523 B1 | 7/2002 | Lafontaine |
| 6,428,552 B1 | 8/2002 | Sparks |
| 6,432,127 B1 | 8/2002 | Kim et al. |
| 6,447,539 B1 | 9/2002 | Nelson et al. |
| 6,475,226 B1 | 11/2002 | Belef et al. |
| 6,485,458 B1 | 11/2002 | Takahashi |
| 6,491,660 B2 | 12/2002 | Guo et al. |
| 6,491,707 B2 | 12/2002 | Makower et al. |
| 6,506,178 B1 | 1/2003 | Schubart et al. |
| 6,508,824 B1 | 1/2003 | Flaherty et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,544,230 B1 | 4/2003 | Flaherty et al. |
| 6,561,998 B1 | 5/2003 | Roth et al. |
| 6,565,583 B1 | 5/2003 | Deaton |
| 6,569,129 B1 | 5/2003 | Holmes, Jr. et al. |
| 6,569,143 B2 | 5/2003 | Alchas et al. |
| 6,569,145 B1 | 5/2003 | Shmulewitz et al. |
| 6,569,150 B2 | 5/2003 | Teague et al. |
| 6,579,311 B1 | 6/2003 | Makower |
| 6,589,164 B1 | 7/2003 | Flaherty |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |
| 6,623,448 B2 | 9/2003 | Slater |
| 6,638,247 B1 | 10/2003 | Selmon et al. |
| 6,638,293 B1 | 10/2003 | Makower et al. |
| 6,655,386 B1 | 12/2003 | Makower et al. |
| 6,656,195 B2 | 12/2003 | Peters et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,444 B1 | 3/2004 | Makower |
| 6,719,725 B2 | 4/2004 | Milo et al. |
| 6,726,677 B1 | 4/2004 | Flaherty et al. |
| 6,746,426 B1 | 6/2004 | Flaherty et al. |
| 6,746,462 B1 | 6/2004 | Selmon et al. |
| 6,746,464 B1 | 6/2004 | Makower |
| 6,786,884 B1 | 9/2004 | DeCant, Jr. et al. |
| 6,800,085 B2 | 10/2004 | Selmon et al. |
| 6,824,550 B1 | 11/2004 | Noriega et al. |
| 6,830,577 B2 | 12/2004 | Nash et al. |
| 6,837,868 B1 | 1/2005 | Fajnsztajn |
| 6,860,892 B1 | 3/2005 | Tanaka |
| 6,863,684 B2 | 3/2005 | Kim et al. |
| 6,866,676 B2 | 3/2005 | Kieturakis et al. |
| 6,884,225 B2 | 4/2005 | Kato et al. |
| 6,905,505 B2 | 6/2005 | Nash et al. |
| 6,929,009 B2 | 8/2005 | Makower et al. |
| 6,936,056 B2 | 8/2005 | Nash et al. |
| 6,942,641 B2 | 9/2005 | Seddon |
| 6,949,125 B2 | 9/2005 | Robertson |
| 6,991,617 B2 | 1/2006 | Hektner et al. |
| 7,004,173 B2 | 2/2006 | Sparks et al. |
| 7,056,325 B1 | 6/2006 | Makower et al. |
| 7,059,330 B2 | 6/2006 | Makower et al. |
| 7,083,588 B1 | 8/2006 | Shmulewitz et al. |
| 7,094,230 B2 | 8/2006 | Flaherty et al. |
| 7,105,031 B2 | 9/2006 | Letort |
| 7,134,438 B2 | 11/2006 | Makower et al. |
| 7,137,990 B2 | 11/2006 | Hebert et al. |
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Ganbotto et al. |
| 7,377,910 B2 | 5/2008 | Katoh et al. |
| 7,465,286 B2 | 12/2008 | Patterson et al. |
| 2001/0000041 A1 | 3/2001 | Selmon et al. |
| 2001/0056273 A1 | 12/2001 | C |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1 | 6/2003 | Jen et al. |
| 2003/0120195 A1 | 6/2003 | Milo et al. |
| 2003/0167038 A1 | 9/2003 | Yozu et al. |
| 2003/0236542 A1 | 12/2003 | Makower |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1 | 8/2004 | Simpson et al. |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |

(56) References Cited

U.S. PATENT DOCUMENTS

| | | | |
|---|---|---|---|
| 2005/0096568 A1* | 5/2005 | Kato | A61M 25/09 600/585 |
| 2005/0171478 A1 | 8/2005 | Selmon et al. | |
| 2005/0177105 A1 | 8/2005 | Shalev | |
| 2005/0216044 A1 | 9/2005 | Hong | |
| 2005/0261663 A1 | 11/2005 | Patterson et al. | |
| 2006/0009715 A1* | 1/2006 | Khairkhahan | A61B 17/32037 600/585 |
| 2006/0094930 A1 | 5/2006 | Sparks et al. | |
| 2006/0135984 A1 | 6/2006 | Kramer et al. | |
| 2006/0200047 A1* | 9/2006 | Galdonik | A61M 25/0138 600/585 |
| 2006/0229646 A1 | 10/2006 | Sparks | |
| 2006/0271078 A1 | 11/2006 | Modesitt | |
| 2006/0293612 A1 | 12/2006 | Jenson et al. | |
| 2007/0083220 A1 | 4/2007 | Shamay | |
| 2007/0088230 A1 | 4/2007 | Terashi et al. | |
| 2007/0093779 A1 | 4/2007 | Kugler et al. | |
| 2007/0093780 A1 | 4/2007 | Kugler et al. | |
| 2007/0093781 A1 | 4/2007 | Kugler et al. | |
| 2007/0093782 A1 | 4/2007 | Kugler et al. | |
| 2007/0093783 A1 | 4/2007 | Kugler et al. | |
| 2007/0191778 A1* | 8/2007 | Venbrux | A61M 25/09 604/164.13 |
| 2007/0265596 A1 | 11/2007 | Jen et al. | |
| 2008/0097247 A1* | 4/2008 | Eskuri | A61M 25/09 600/585 |
| 2008/0103443 A1 | 5/2008 | Kabrick et al. | |
| 2008/0228171 A1 | 9/2008 | Kugler et al. | |
| 2008/0243065 A1 | 10/2008 | Rottenberg et al. | |
| 2008/0243067 A1 | 10/2008 | Rottenberg et al. | |
| 2009/0088685 A1 | 4/2009 | Kugler et al. | |
| 2009/0124899 A1 | 5/2009 | Jacobs et al. | |
| 2009/0198153 A1* | 8/2009 | Shriver | 600/585 |
| 2009/0209910 A1 | 8/2009 | Kugler et al. | |
| 2009/0270890 A1 | 10/2009 | Robinson et al. | |
| 2010/0063534 A1 | 3/2010 | Kugler et al. | |

FOREIGN PATENT DOCUMENTS

| | | |
|---|---|---|
| EP | 820782 B1 | 1/2002 |
| EP | 868924 B1 | 12/2004 |
| JP | 08257136 A | 10/1996 |
| JP | 2007-089901 A | 4/2007 |
| WO | 9839041 A1 | 9/1998 |
| WO | 0178822 A9 | 12/2002 |
| WO | 2008063621 A9 | 8/2008 |
| WO | 2007033052 A3 | 4/2009 |
| WO | 2009054943 A1 | 4/2009 |
| WO | 2009100129 A3 | 10/2009 |
| WO | 2009134346 A3 | 1/2010 |
| WO | 2010019241 A1 | 2/2010 |
| WO | 2010044816 A1 | 4/2010 |

* cited by examiner

ENDOVASCULAR DEVICE WITH A TISSUE PIERCING DISTAL PROBE AND ASSOCIATED METHODS

CROSS-REFERENCE TO RELATED APPLICATIONS

This application is a continuation of U.S. patent application Ser. No. 12/461,261, filed on Aug. 5, 2009, which claims the benefit of U.S. Provisional Application No. 61/104,868, filed on Oct. 13, 2008. U.S. patent application Ser. No. 12/461,261 is a continuation-in-part of application U.S. patent application Ser. No. 12/320,792, filed on Feb. 4, 2009, now U.S. Pat. No. 8,202,246, which claims the benefit of U.S. Provisional Application No. 61/063,756, filed on Feb. 5, 2008. The contents of the above-noted applications are expressly incorporated herein by reference in their entirety.

FIELD OF THE INVENTION

The inventions described herein relate to devices and associated methods for the treatment of chronic total occlusions. More particularly, the inventions described herein relate to devices and methods for crossing chronic total occlusions and establishing a pathway blood flow past the chronic total occlusions.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, cannot accurately direct endovascular devices toward the visualized lumen, or fail to advance devices through the lesion. Bypass surgery is often the preferred treatment for patients with chronic total occlusions, but less invasive techniques would be preferred.

BRIEF SUMMARY

Devices, systems and methods for treating diseases and disorders effecting the cardiovascular system of the human body are disclosed. An exemplary blood vessel in accordance with this disclosure comprises a shaft, tip member fixed to the shaft, and a probe extending beyond a distal surface of the tip member. In some useful embodiments, the tip member is relatively atraumatic and the probe is shaped so as to be more likely to produce trauma than the tip member.

BRIEF DESCRIPTION OF THE FIGURES

In FIG. 2, a total occlusion is shown within a coronary artery.

In FIG. 3, the wall of the blood vessel is shown having three layers (the intima, the media, and the adventitia).

In FIG. 4, an orienting device is shown disposed between the adventitia and the intima of the artery.

FIG. 14 is enlarged and simplified relative to the items shown in FIG. 13.

FIG. 19 has a different scale than the previous figure so that more of the surrounding context is visible in FIG. 19. In FIG. 19, the distal end of the re-entry device can be seen residing in the true lumen of the blood vessel.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
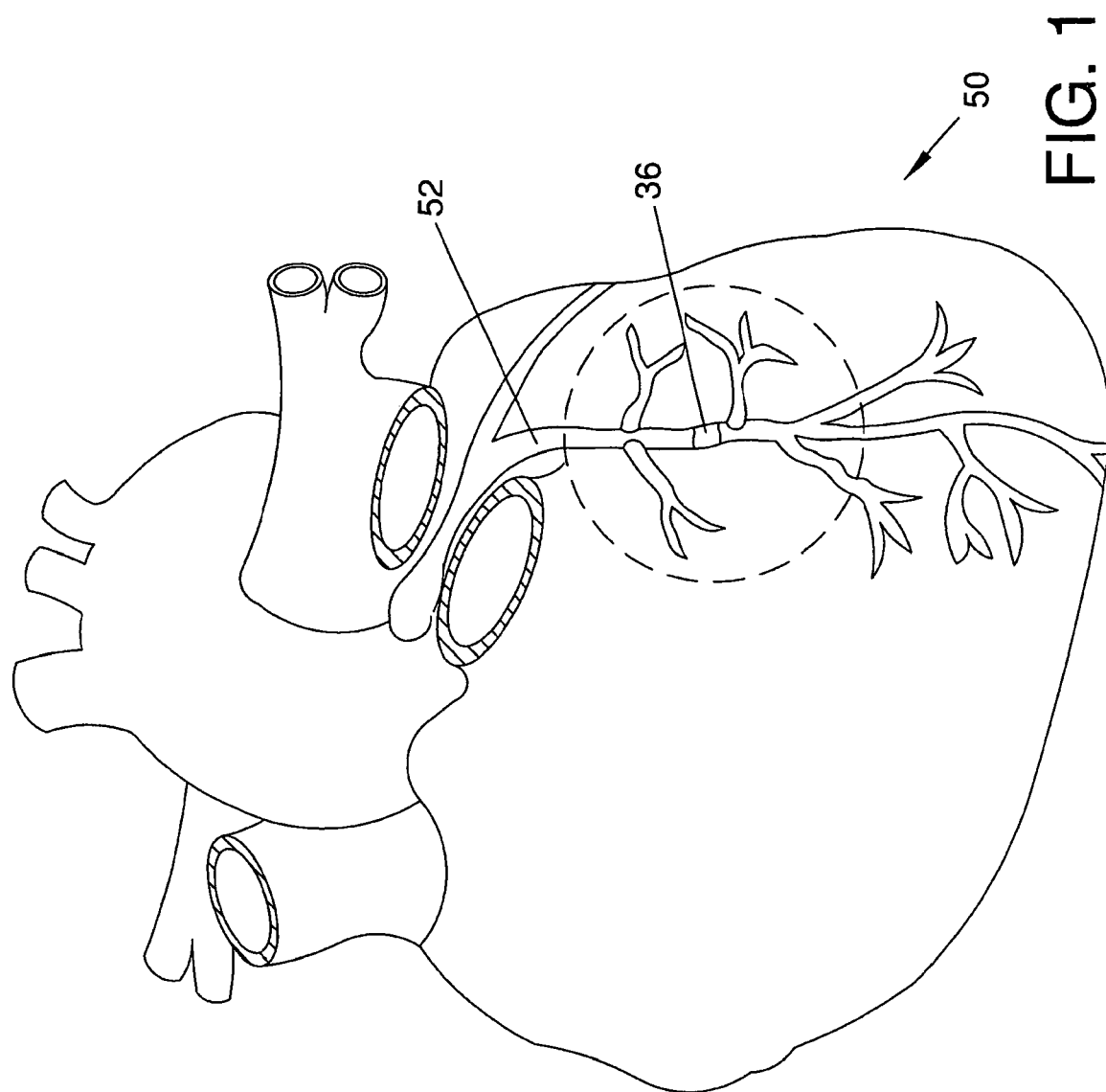
FIG. 1 is a somewhat stylized representation of a human heart. The heart includes a plurality of coronary arteries, all of which are susceptible to occlusion.

FIG. 1 is a somewhat stylized representation of a human heart 50. Heart 50 includes a plurality of coronary arteries 52, all of which are susceptible to occlusion. Under certain physiological circumstances and given sufficient time, some occlusions may become total or complete, such as total occlusion 36 shown in FIG. 1.

As used herein, the terms total occlusion and complete occlusion are intended to refer to the same or similar degree of occlusion with some possible variation in the age of the occlusion. Generally, a total occlusion refers to a vascular lumen that is ninety percent or more functionally occluded in cross-sectional area, rendering it with little to no blood flow therethrough and making it difficult or impossible to pass a conventional guide wire therethrough. Also generally, the older the total occlusion the more organized the occlusive material will be and the more fibrous and calcified it will become. According to one accepted clinical definition, a total occlusion is considered chronic if it is greater than two weeks old from symptom onset.

Figure 2:
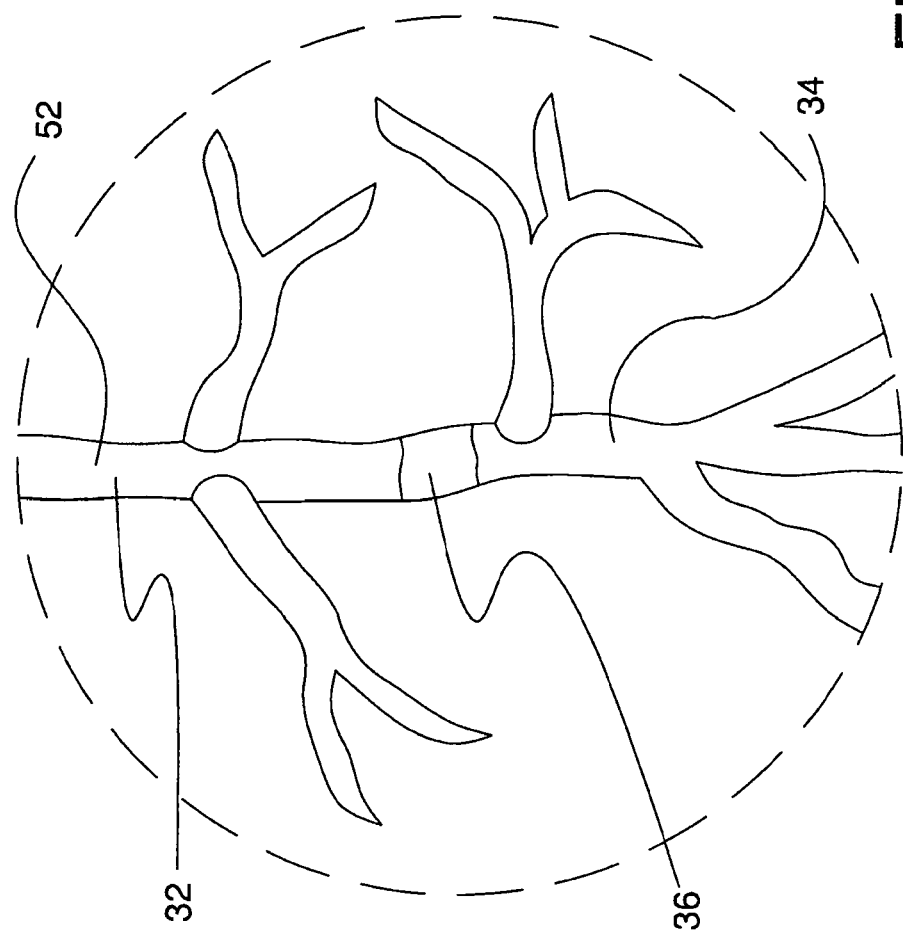
FIG. 2 is an enlarged view further illustrating a portion of the heart shown in the previous figure.

FIG. 2 is an enlarged view further illustrating a portion of heart 50 shown in the previous figure. In FIG. 2, a total occlusion 36 is shown within a coronary artery 52. Generally, the proximal segment 32 of artery 52 (i.e., the portion of artery 52 proximal of total occlusion 36) has adequate blood flow to supply the surrounding cardiac muscle and may be easily accessed using endovascular devices. In contrast, the distal segment 34 of artery 52 (i.e., the portion of artery 52 distal of total occlusion 36) is not easily accessed with interventional devices. Additionally, distal segment 34 has significantly reduced blood flow as compared to proximal segment 32.

Figure 3:
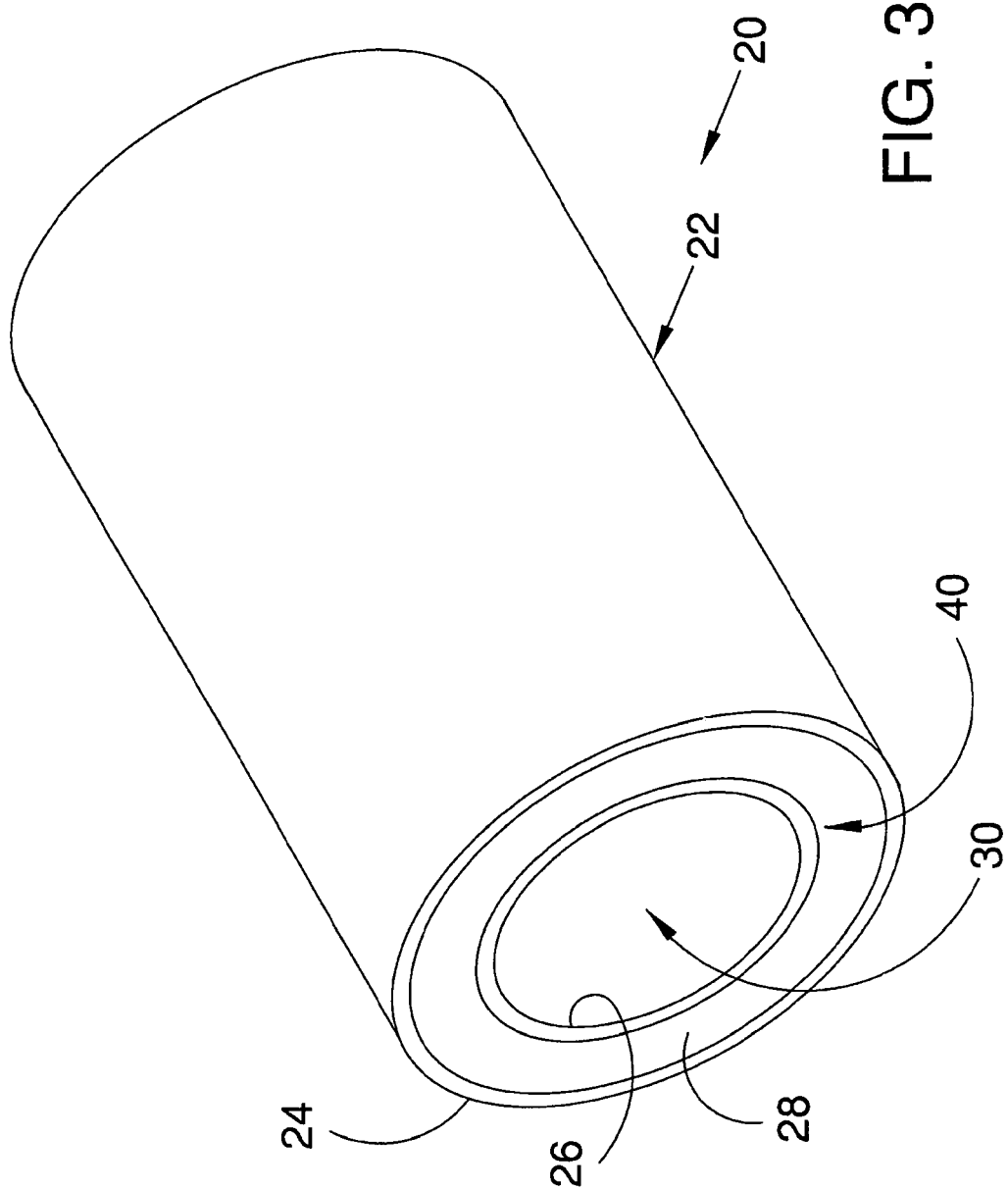
FIG. 3 is a perspective view of a blood vessel (e.g., a coronary artery).

FIG. 3 is a perspective view of an artery 20 having a wall 22. In FIG. 3, wall 22 of artery 20 is shown having three layers. The outermost layer of wall 22 is the adventitia 24 and the innermost layer of wall 22 is the intima 26. Intima 26 defines a true lumen 30 of artery 20. The tissues extending between intima 26 and adventitia 24 may be collectively referred to as the media 28. For purposes of illustration, intima 26, media 28 and adventitia 24 are each shown as a single homogenous layer in FIG. 3. In the human body, however, the intima and the media each comprise a number of sub-layers. The transition between the external most portion of the intima and the internal most portion of the media is sometimes referred to as the subintimal space 40.

With reference to FIG. 3, it will be appreciated that the subintimal space 40 has a generally annular shape with its radial center at the center of the true lumen. Some of the devices and methods discussed in this detailed description may take advantage of the position and geometry of the subintimal space 40 relative to the true lumen of the blood vessel. For example, some orienting devices described herein may be adapted to orient themselves within that space. Once the orientation of the orienting device is established, the orienting device may be used to direct a re-entry device toward the true lumen.

Figure 4:
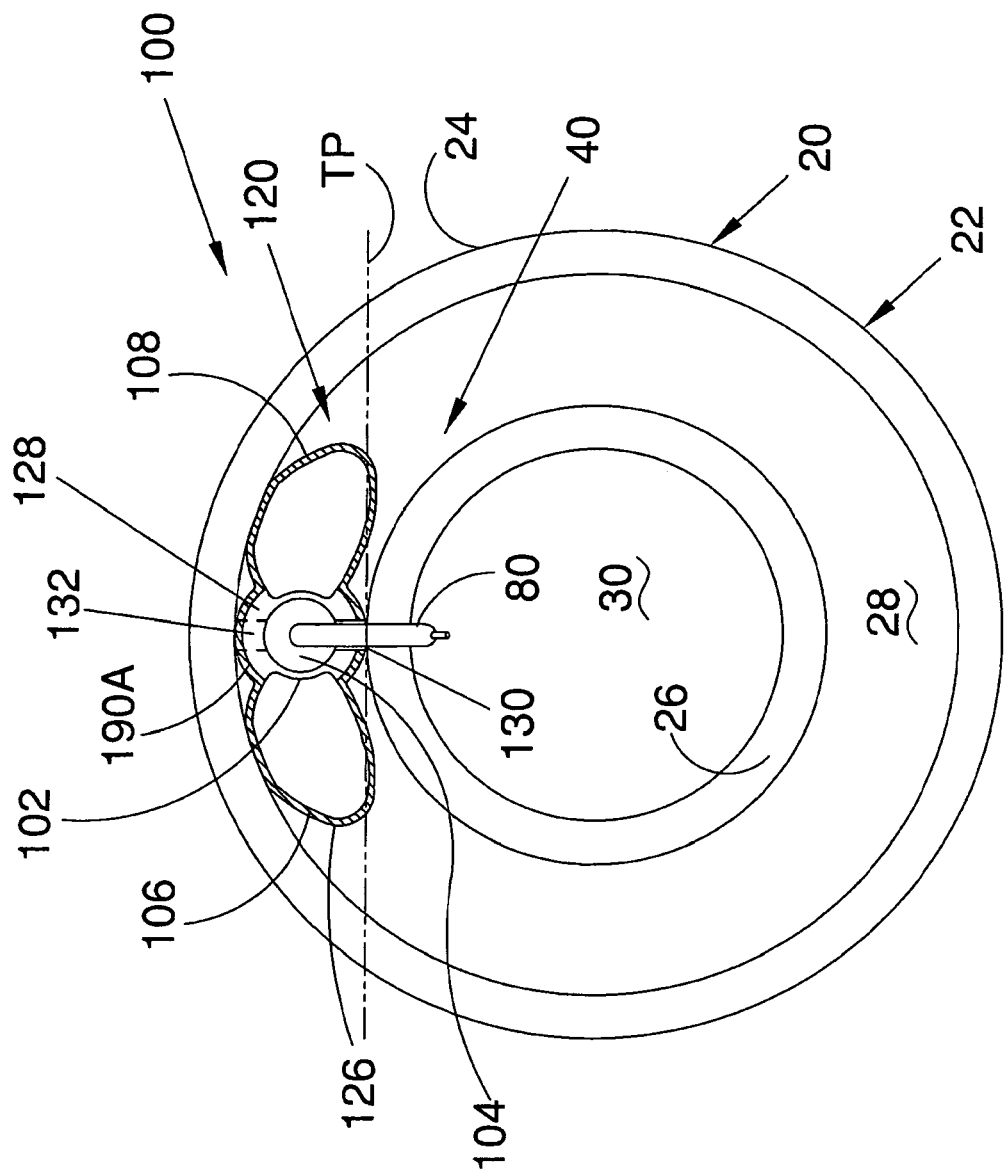
FIG. 4 is a lateral cross-sectional view of the artery shown in the previous figure.

FIG. 4 is a lateral cross-sectional view of artery 20 shown in the previous figure. In FIG. 4, an orienting device 100 is shown disposed between adventitia 24 and intima 26 of artery 20. Orienting device 100 comprises a distal shaft 102 having an outer wall 128 defining a central lumen 104. Orienting device 100 comprises an orienting element 120 that is coupled to distal shaft 102.

In the embodiment of FIG. 4, orienting element 120 comprises an inflatable member 126. The top of inflatable member 126 may be fixed to distal shaft 102, for example, at a first interface 190A. The bottom of inflatable member 126 may be fixed to distal shaft 102, for example, at a second interface 190B.

Orienting element 120 comprises a first portion 106 and a second portion 108. First portion 106 of orienting element 120 extends in a first direction away from distal shaft 102. Second portion 108 of orienting element 120 extends away from distal shaft 102 in a second direction that is generally opposite the first direction.

Distal shaft 102 defines a first aperture 130 and a second aperture 132. First aperture 130 extends in a third direction through distal shaft 102. Second aperture 132 extends through distal shaft 102 in a forth direction that is generally opposite the third direction. First aperture 130 and second aperture 132 are generally oriented at a right angle to a tangent plane TP. In FIG. 4, tangent plane TP is tangent to subintimal space 40.

When inflatable member 126 is inflated, the number of directions that first aperture 130 and second aperture 132 may be facing is reduced. This may be conceptualized in terms of degrees of freedom. When inflatable member 126 of orienting element 120 is inflated, the number of directions that an aperture may be facing is reduced from 360 degrees of freedom to two degrees of freedom, 180 degrees apart.

When inflatable member 126 of orienting element 120 is inflated between adventitia 24 and intima 26 of artery 20 orienting device 100 will orient itself within artery 20 so that either first aperture 130 or second aperture 132 opens toward a true lumen 30 of artery 20. In the embodiment of FIG. 4, orienting device 100 has been positioned so that first aperture 130 opens toward intima 26 of artery 20 and second aperture 132 opens toward adventitia 24. In FIG. 4, a re-entry device 180 is shown extending through first aperture 130 and intima 26. A distal end of re-entry device 180 is disposed in true lumen 30 of blood vessel 20. Orienting device 100 and re-entry device 180 may be used to establish fluid communication between a proximal segment and a distal segment that are separated by an occlusion. Exemplary methods for establishing this fluid communication will be described below.

Figure 5:
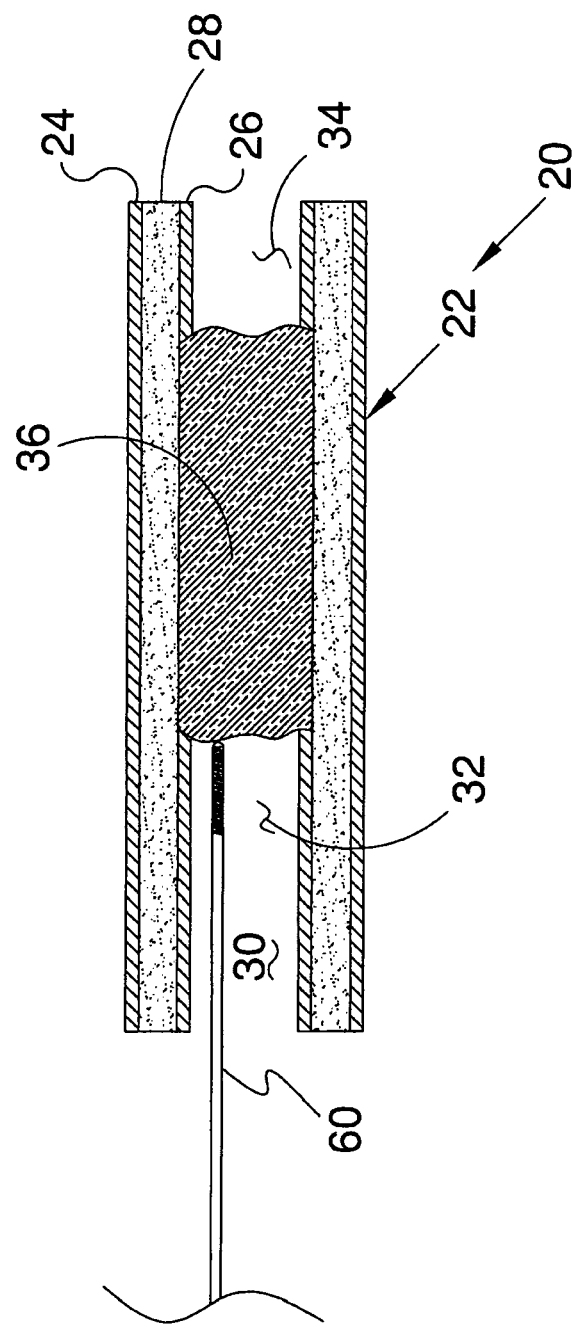
FIG. 5 is a longitudinal cross-sectional view of an artery having an occlusion blocking the true lumen.

FIG. 5 is a longitudinal cross-sectional view of an artery 20 having an occlusion 36 blocking true lumen 30 thereof. Occlusion 36 divides true lumen 30 into a proximal segment 32 and a distal segment 34. In FIG. 5, a distal portion of a guidewire 60 is shown extending into proximal segment 32 of true lumen 30. The methods described in this document may include the step of advancing a guidewire to a location proximate an occlusion in a blood vessel. The exemplary methods described in this document may also include the step of advancing guidewire 60 between occlusion 36 and adventitia 24 of wall 22. In some cases, however, the nature of the occlusion and the blood vessel will be such that the guidewire is unlikely to advance beyond the occlusion. When this is the case, the guidewire may be used to guide additional endovascular devices to a location proximate occlusion 36.

Figure 6:
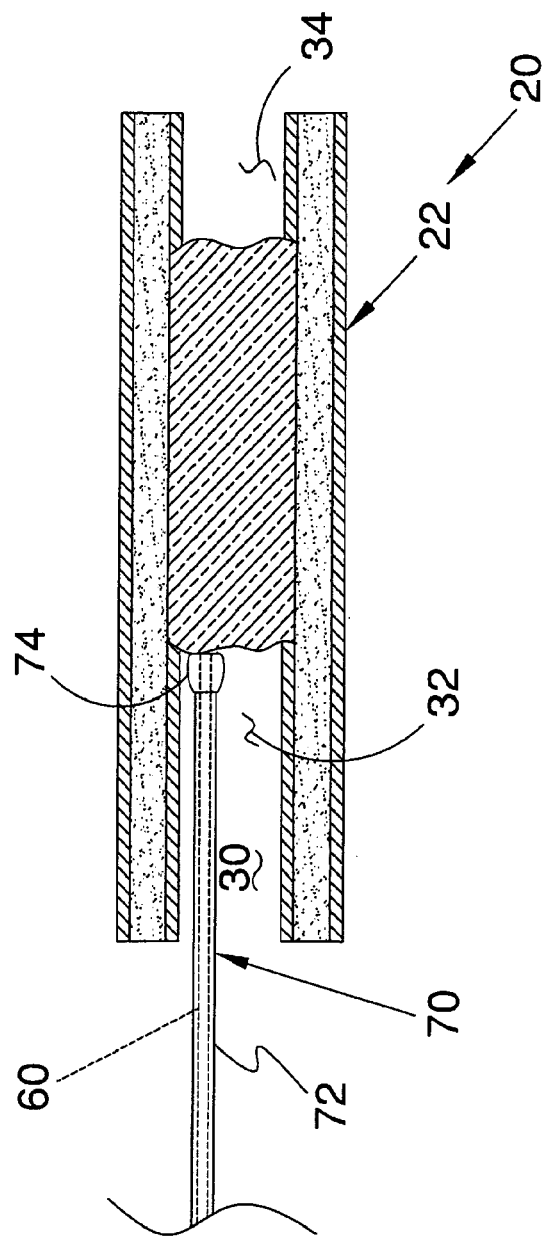
FIG. 6 is an additional cross-sectional view of the artery shown in the previous figure. In the embodiment of FIG. 6, a crossing device has been advanced over a guidewire so that a distal portion of crossing device is disposed in proximal segment of the true lumen.

FIG. 6 is an additional cross-sectional view of artery 20 shown in the previous figure. In the embodiment of FIG. 6, a crossing device 70 has been advanced over guidewire 60 so that a distal portion of crossing device 70 is disposed in proximal segment 32 of true lumen 30. Crossing device 70 of FIG. 6 comprises a tip 74 that is fixed to a distal end of a shaft 72. Crossing device 70 may be used in conjunction with a method for establishing a channel between proximal segment 32 and distal segment 34. The methods described in this document may include the step of advancing a crossing device over a guidewire.

In some useful methods in accordance with the present disclosure, crossing device 70 may be rotated about it's longitudinal axis and moved in a direction parallel to it's longitudinal axis simultaneously. When this is the case, rotation of crossing device 70 may reduce resistance to the axial advancement of crossing device 70. These methods take advantage of the fact that the kinetic coefficient of friction is usually less than the static coefficient of friction for a given frictional interface. Rotating crossing device 70 assures that the coefficient of friction at the interface between the crossing device and the surround tissue will be a kinetic coefficient of friction and not a static coefficient of friction.

Figure 7:
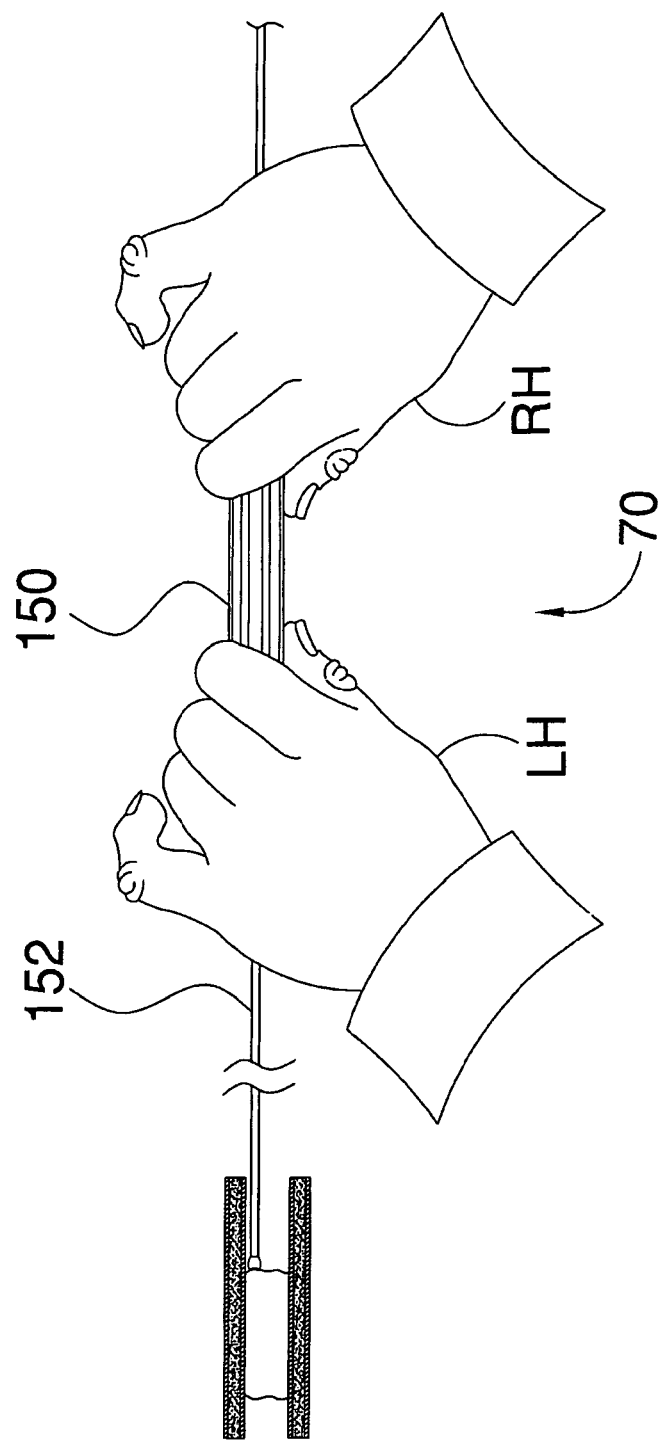
FIG. 7 is a plan view showing an assembly including crossing device shown in the previous figure.

FIG. 7 is a plan view showing an assembly including crossing device 70 shown in the previous figure. In the embodiment of FIG. 7, a handle assembly 76 is coupled to crossing device 70. In FIG. 7, handle assembly 76 is shown disposed about a proximal portion of a shaft 152 of crossing device 70. In FIG. 7, a portion of handle assembly 76 is positioned between the thumb and forefinger of a left hand LH. A second portion of handle assembly 76 is disposed between the thumb and forefinger of a right hand RH. With reference to FIG. 7, it will be appreciated that handle assembly 76 is long enough to receive the thumb and forefingers of a physician's right and left hands. When this is the case, a physician can use two hands to rotate handle assembly 76.

Rotation of crossing device 70 can be achieved by rolling handle assembly 76 between the thumb and forefinger of one hand. Two hands may also be used to rotate handle assembly 76 as shown in FIG. 7. In some useful methods, crossing device 70 can be rotated and axially advanced simultaneously.

In some useful methods in accordance with the present disclosure, crossing device 70 is rotated at a rotational speed of between about 2 revolutions per minute and about 200 revolutions per minute. In some particularly useful methods in accordance with the present disclosure, crossing device 70 is rotated at a rotational speed of between about 50 revolutions per minute and about 150 revolutions per minute.

Crossing device 70 may be rotated by hand as depicted in FIG. 7. It is also contemplated that a mechanical device (e.g., an electric motor) may be used to rotate crossing device 70. Rotating crossing device 70 assures that the coefficient of friction at the interface between the crossing device and the surround tissue will be a kinetic coefficient of friction and not a static coefficient of friction.

Figure 8:
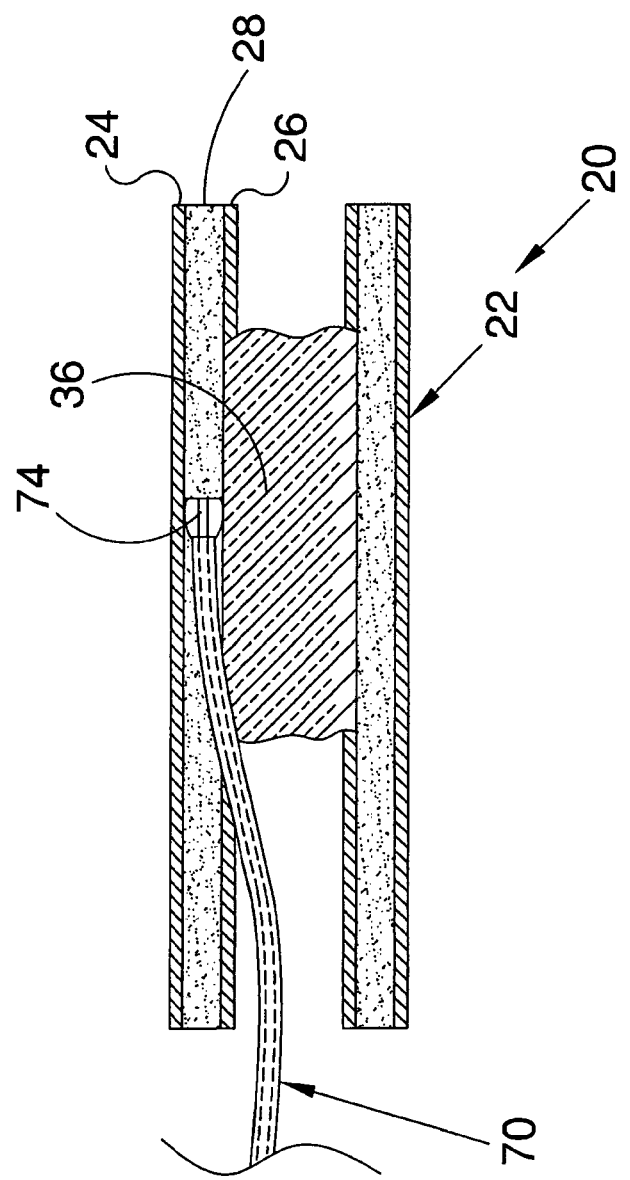
FIG. 8 is an additional view of an artery. In the embodiment of FIG. 8, the distal end of the crossing device has been advanced in a distal direction so that the tip of the crossing device is adjacent an occlusion that is blocking the true lumen of the artery.

FIG. 8 is an additional longitudinal cross-sectional view of artery 20. In the embodiment of FIG. 8, the distal end of crossing device 70 has been advanced in a distal direction so that tip 74 is adjacent occlusion 36. With reference to FIG. 8, it will be appreciated that tip 74 has passed beyond intima 26 and is disposed between occlusion 36 and adventitia 24 of artery 20. Some methods described in this document may include the step of advancing a crossing device between an occlusion and the adventitia of an artery.

Figure 9:
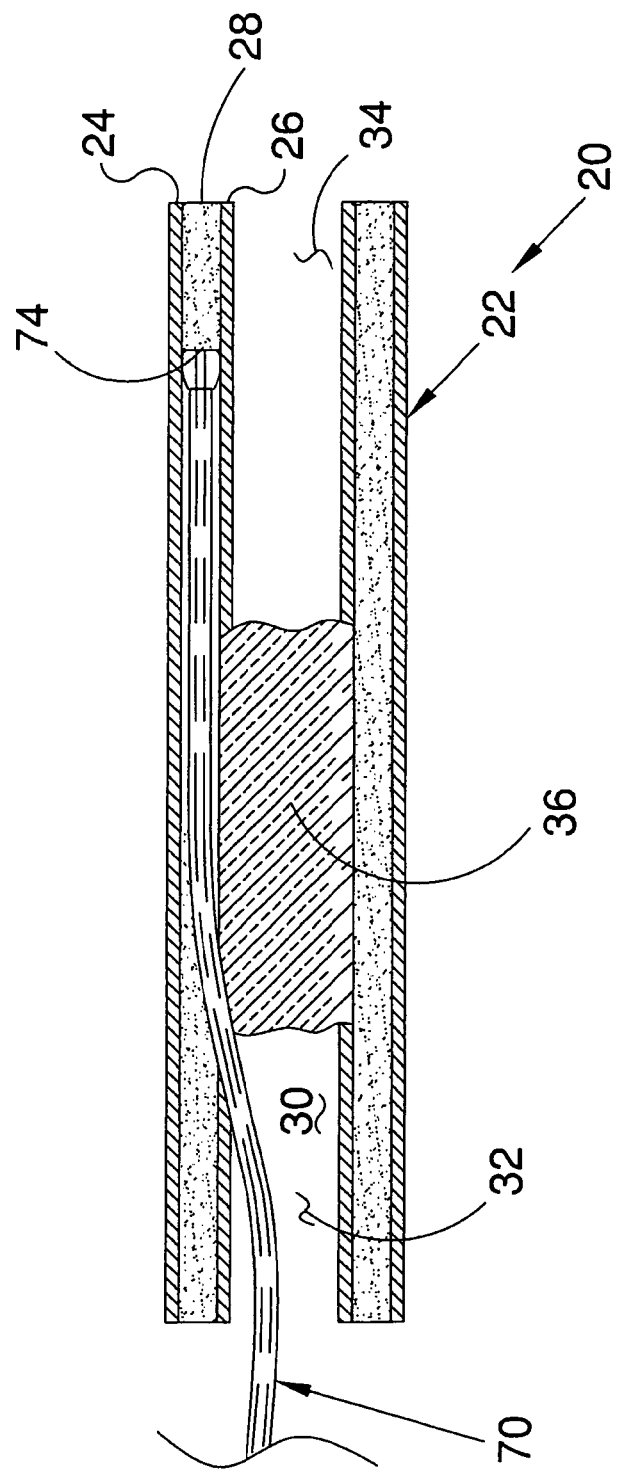
FIG. 9 is an additional view of the artery and the crossing device shown in the previous figure. In the embodiment of FIG. 9, the distal end of the crossing device has been advanced between the intima and the adventitia of the wall of the artery.

FIG. 9 is an additional view of artery 20 and crossing device 70 shown in the previous figure. In the embodiment of FIG. 9, the distal end of crossing device 70 has been advanced in an axial direction past occlusion 36. Methods described herein may include the step of advancing a crossing device beyond an occlusion. In the embodiment of FIG. 9, crossing device has crossed occlusion 36 by advancing between occlusion 36 and adventitia 24 of wall 22.

It is to be appreciated that other methods of crossing an occlusion are within the spirit and scope of this disclosure. For example, the crossing device 70 may pass through occlusion 36 while remaining disposed inside true lumen 30. In FIG. 9, tip 74 of crossing device 70 is shown residing between intima 26 and adventitia 24 of artery 20. As tip 74 moves in an axial direction between intima 26 and adventitia 24, tip 74 may cause blunt dissection of the layers forming wall 22 of artery 20. Alternatively, tip 74 may cause blunt dissection of the materials comprising the occlusion 36.

In the embodiment of FIG. 9, tip 74 of crossing device 70 is disposed between intima 26 and adventitia 24. When this is the case, fluid communication between proximal segment 32 and distal segment 34 may be achieved by creating an opening through intima 26. Such an opening may be created, for example, using a re-entry device and an orienting device that directs the advancement of the re-entry device toward intima 26.

Figure 10:
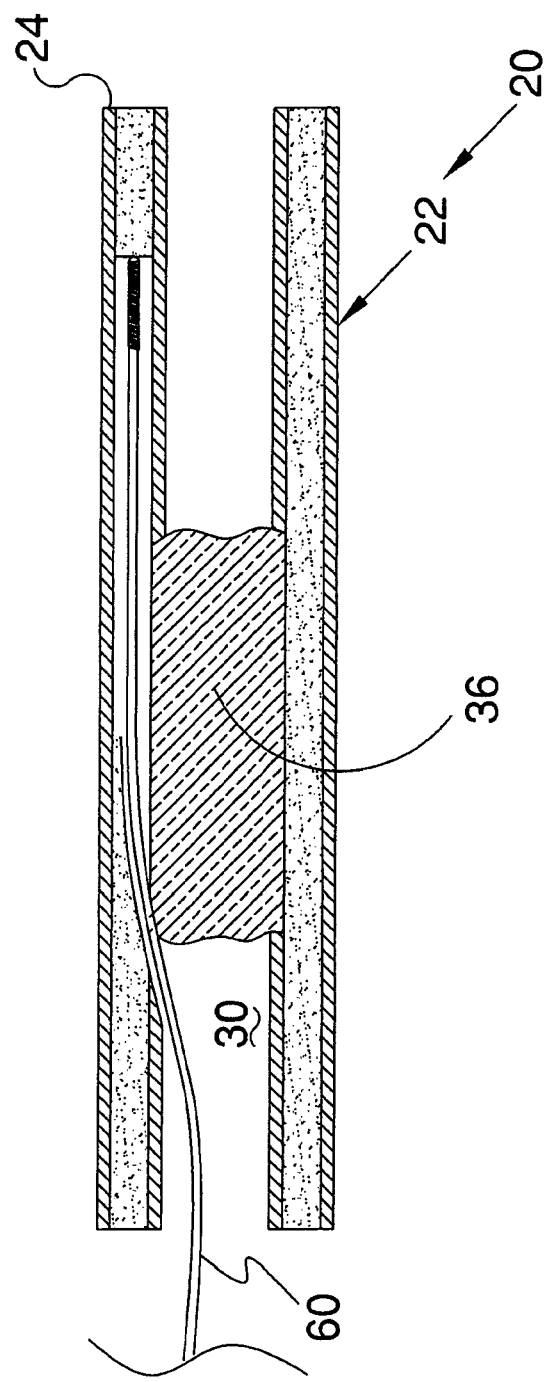
FIG. 10 is an additional view of the artery shown in the previous figure. In the embodiment of FIG. 10, the crossing device has been withdrawn and a guidewire remains in the position formerly occupied by the crossing device.

FIG. 10 is an additional view of artery 20 shown in the previous figure. In the embodiment of FIG. 10, crossing device 70 has been withdrawn from true lumen 30 of artery 20. With reference to FIG. 10, it will be appreciated that guidewire 60 remains in the position formerly occupied by crossing device 70.

The position of guidewire 60 shown in FIG. 10 may be achieved using crossing device 70. Guidewire 60 may be positioned, for example, by first placing crossing device 70 in the position shown in the previous figure, then advancing guidewire 60 through lumen 122 defined by shaft 72 of crossing device 70. Alternately, guidewire 60 may be disposed within lumen 122 while crossing device 70 is advanced beyond occlusion 36.

With guidewire 60 in the position shown in FIG. 10, guidewire 60 may be used to direct other devices between occlusion 36 and adventitia 24. For example, a catheter may be advanced over guidewire 60 until the distal end of the catheter extends between an occlusion and the adventia. After reaching this location, the catheter may be used to dilate the tissue surrounding the catheter. Examples of catheters that may be used to dilate tissue include balloon angioplasty catheters, atherectomy catheters, and stent delivery catheters.

Figure 11:
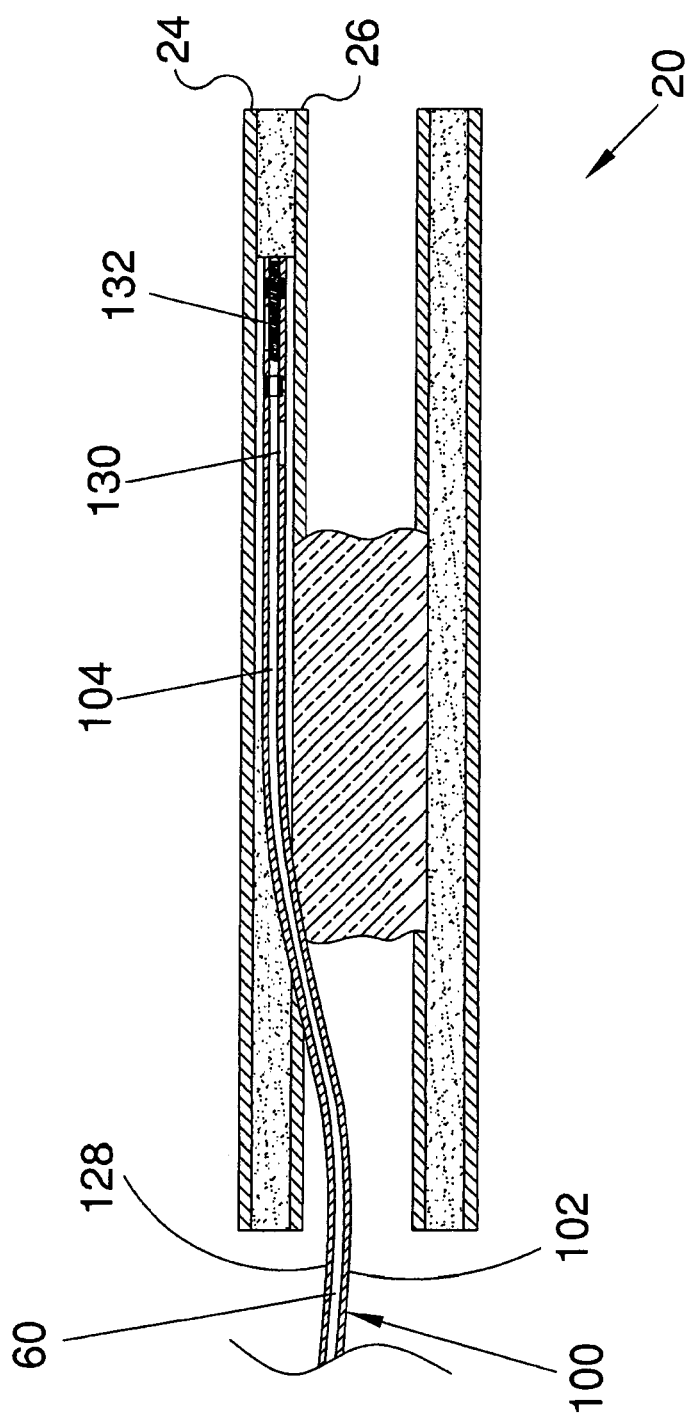
FIG. 11 is an additional view of the artery and the guidewire shown in the previous figure. In the embodiment of FIG. 11, an orienting device 100 been advanced over the guidewire.

FIG. 11 is an additional view of artery 20 and guidewire 60 shown in the previous figure. In the embodiment of FIG. 11, an orienting device 100 has been advanced over guidewire 60. Orienting device 100 includes a distal shaft 102 comprising a outer wall 128 defining a central lumen 104. A first aperture 130 and a second aperture 132 are also defined by outer wall 128. In the embodiment of FIG. 11, first aperture 130 and second aperture 132 are both in fluid communication with central lumen 104.

In the embodiment of FIG. 11, orienting device 100 has been positioned so that first aperture 130 opens toward intima 26 of artery 20 and second aperture 132 opens toward adventitia 24. In the embodiment of FIG. 11, first aperture 130 and second aperture 132 are longitudinally separated from one another. Orienting device 100 includes a first radiopaque marker that is located between first aperture 130 and second aperture 132. A second radiopaque marker of orienting device 100 is located distally of second aperture 132.

Figure 12:
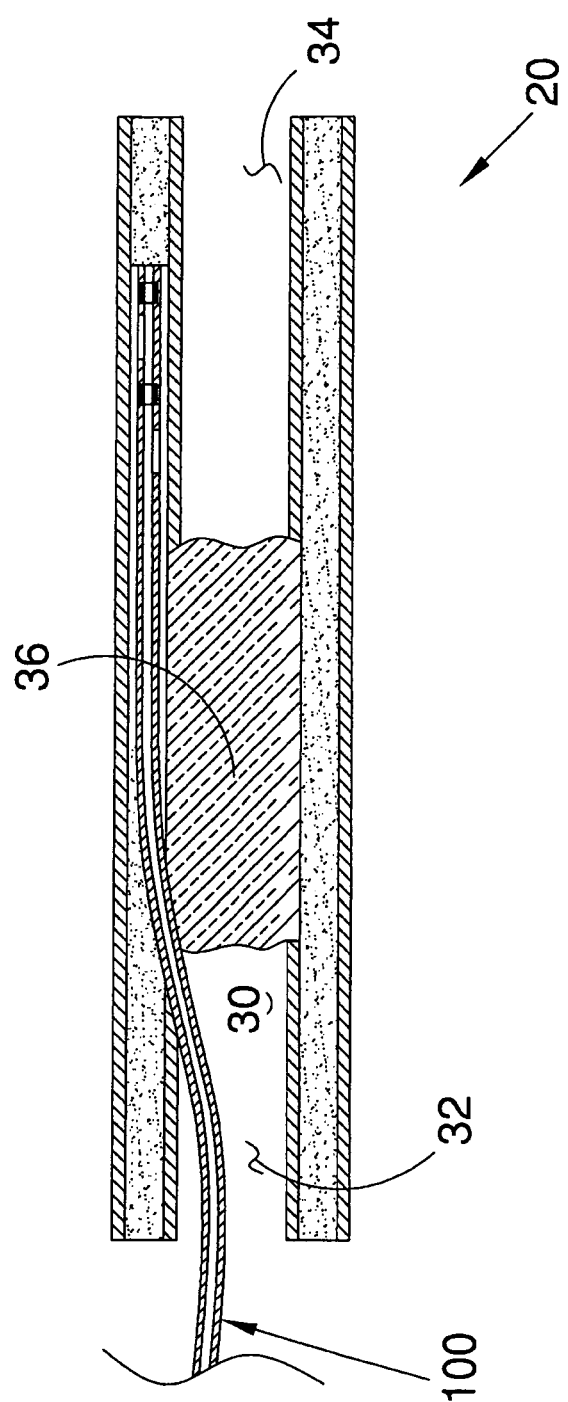
FIG. 12 is an additional view of the artery and the orienting device shown in the previous figure.

FIG. 12 is an additional view of artery 20 and orienting device 100 shown in the previous figure. In the embodiment of FIG. 12, guidewire 60 has been withdrawn leaving orienting device 100 in the position shown in FIG. 12. With reference to FIG. 12, it will be appreciated that orienting device 100 extends beyond occlusion 36. In FIG. 12, occlusion 36 is shown blocking true lumen 30. Occlusion 36 divides true lumen 30 into a proximal segment 32 and a distal segment 34. When an orienting device in accordance with some embodiments disclosed herein is advanced between the adventitia and the intima of an artery, the orienting device may be used to direct a re-entry device toward true lumen 30. Fluid communication between proximal segment 32 and distal segment 34 may be achieved by re-entering the true lumen with a re-entry device.

Figure 13:
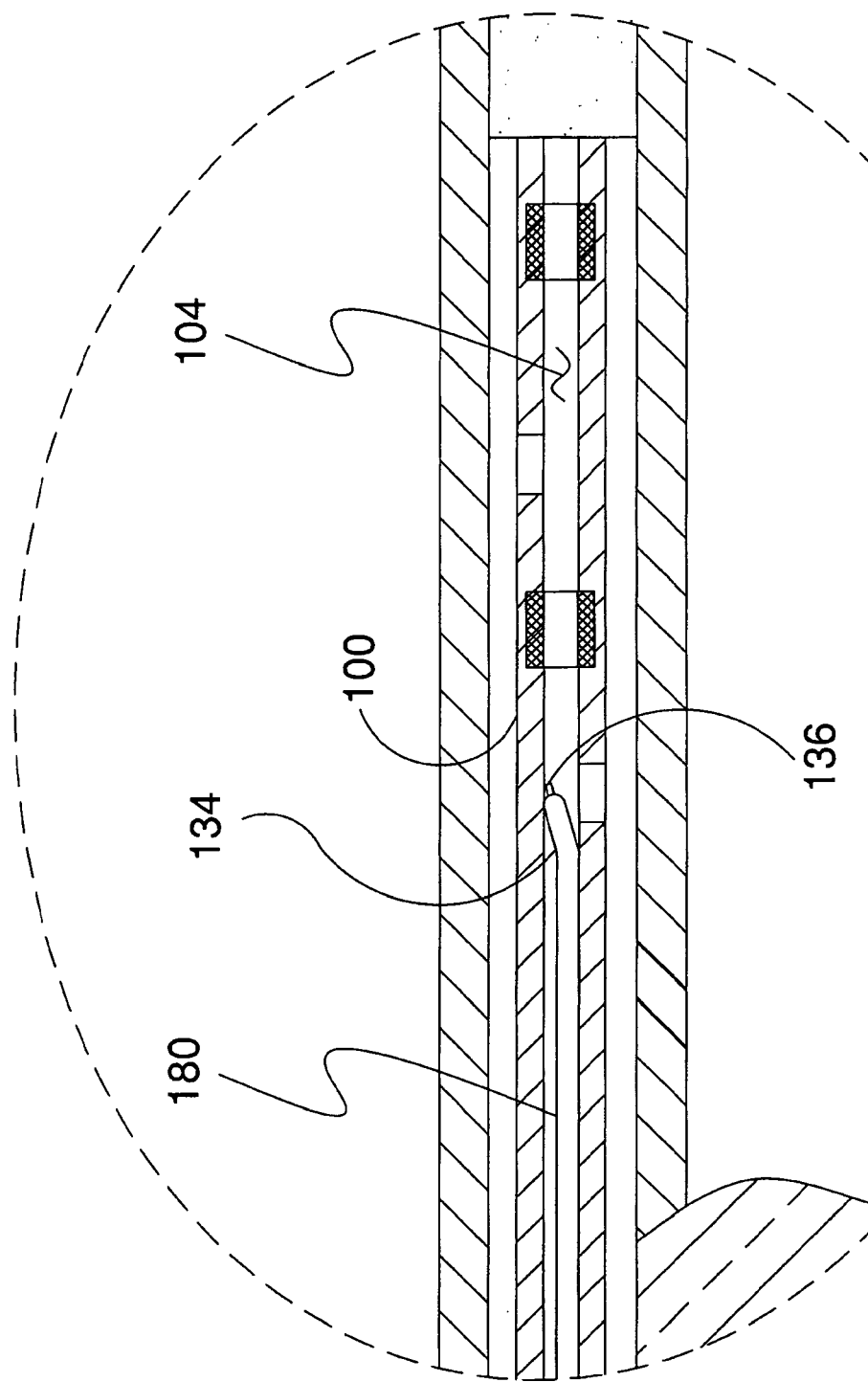
FIG. 13 is an enlarged partial cross-sectional view showing a portion of the orienting device shown in the previous figure. In the embodiment of FIG. 13, a re-entry device has been advanced into the central lumen of orienting device.

FIG. 13 is an enlarged partial cross-sectional view showing a portion of orienting device 100 shown in the previous figure. In the embodiment of FIG. 13, a re-entry device 180 has been advanced into central lumen 104 of orienting device 100. With reference to FIG. 13, it will be appreciated that re-entry device 180 includes a bend 134 near distal end 136 of re-entry device 180.

Figure 14:
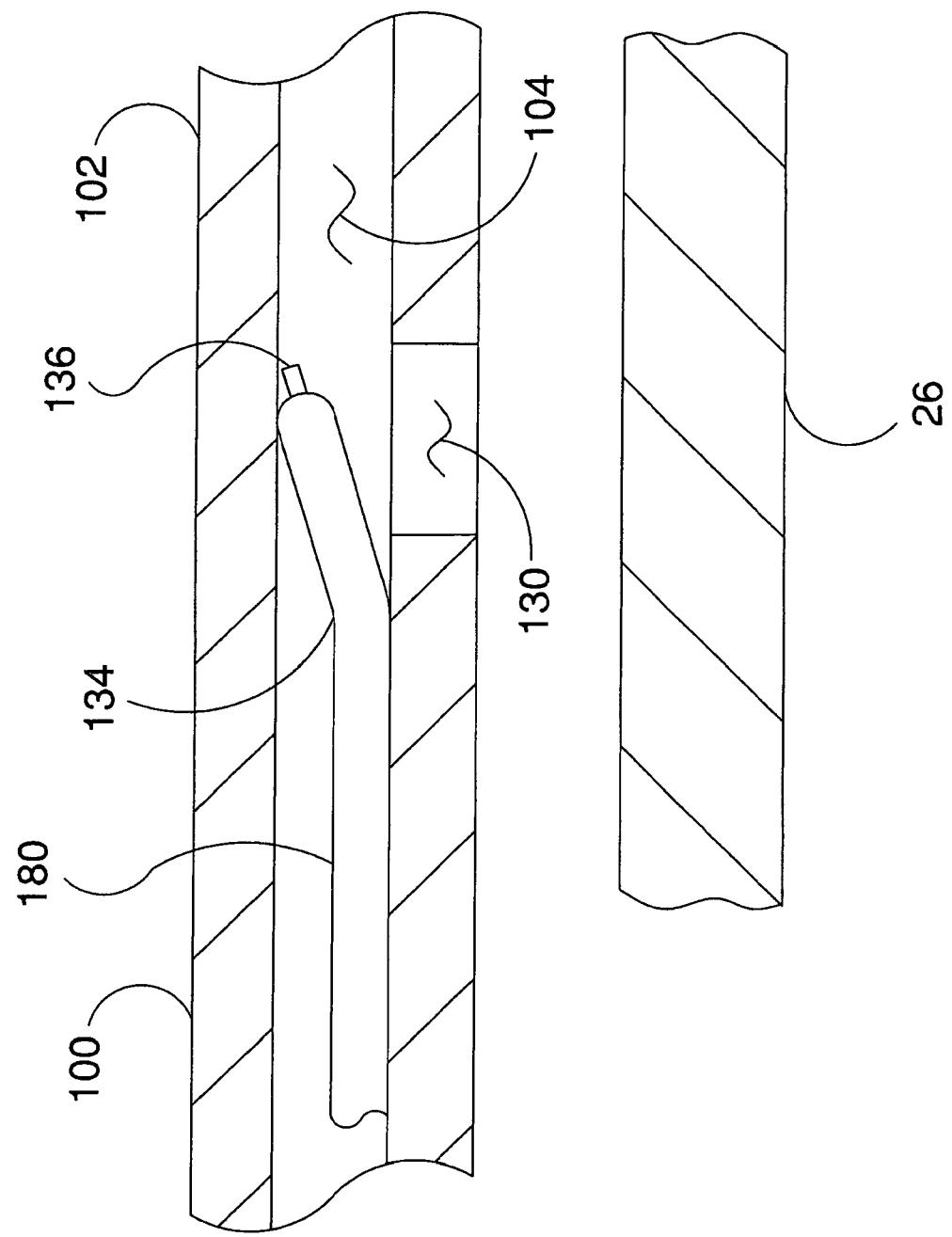
FIG. 14 is an additional partial cross-sectional view showing a portion of the re-entry device and the orienting device shown in FIG. 13. For purposes of illustration.

FIG. 14 is an additional partial cross-sectional view showing a portion of re-entry device 180 and orienting device 100. For purposes of illustration, FIG. 14 is enlarged and simplified relative to the items shown in the previous figure. In the embodiment of FIG. 14, re-entry device 180 is biased to assume a bent shape including a bend 134. Also in the embodiment of FIG. 14, distal shaft 102 of orienting device 100 is holding re-entry device 180 in a somewhat compressed state. When this is the case, re-entry device 180 can be inserted through first aperture 130 by positioning distal end 136 over first aperture 130 and allowing bend 134 to assume it's natural state (i.e., bent at a sharper angle). Re-entry device 180 can be inserted through first aperture 130 until it comes into contact with intima 26.

It the embodiment of FIG. 14, distal end 136 of re-entry device 180 is axially aligned with first aperture 130, however, bend 134 is causing distal end 136 to point away from first aperture 130. When this is the case, distal end 136 may be positioned over first aperture 130 by rotating re-entry device 180 central lumen 104 of orienting device 100.

Figure 15:
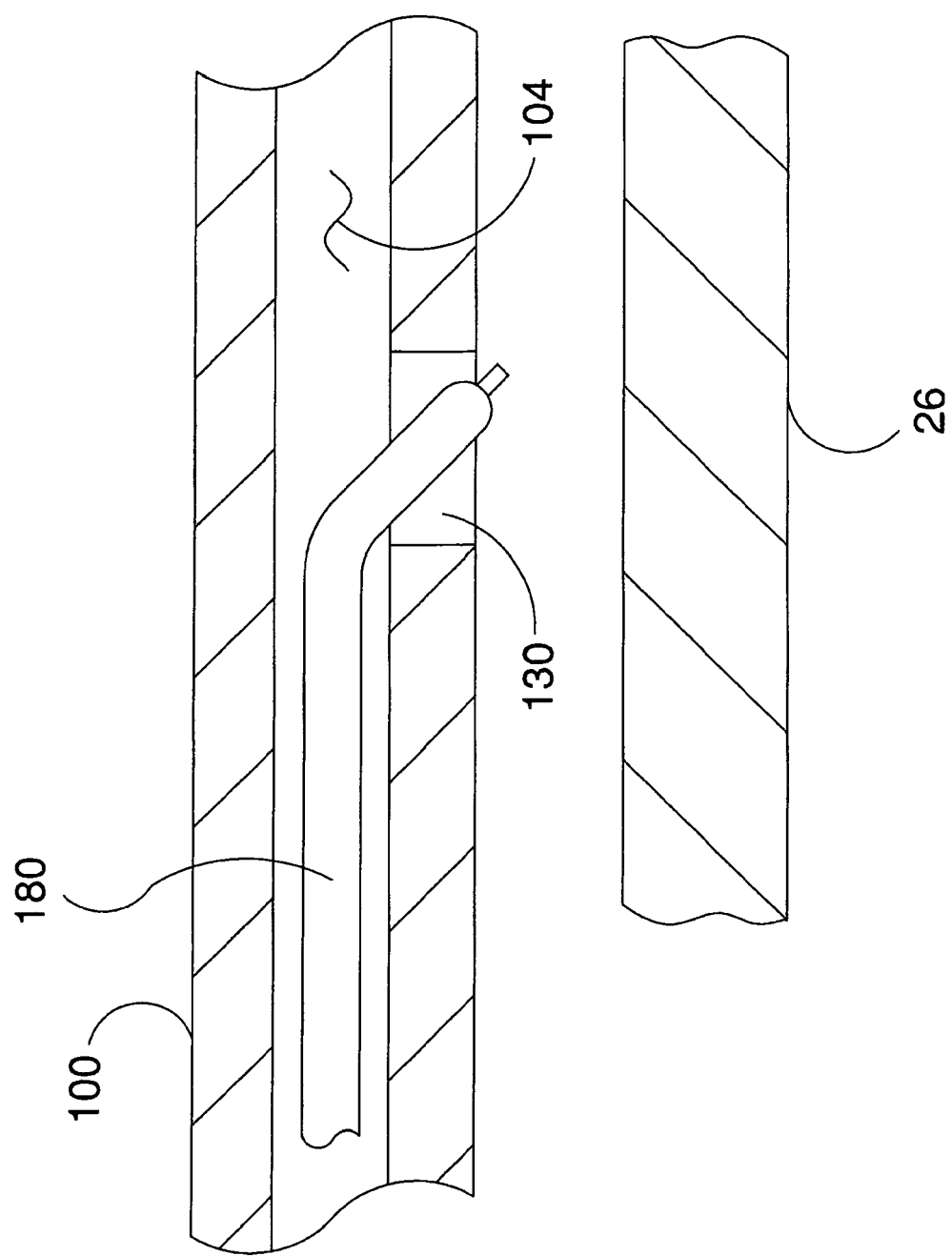
FIG. 15 is an enlarged partial cross-sectional view showing a portion of the re-entry device and the orienting device shown in the previous figure. In the embodiment of FIG. 15, the re-entry device has been positioned so that a distal portion of the re-entry device has entered the first aperture of the orienting device.

FIG. 15 is an enlarged partial cross-sectional view showing a portion of re-entry device 180 and orienting device 100 shown in the previous figure. In the embodiment of FIG. 15, re-entry device 180 has been positioned so that a distal portion of reentry device 180 has entered first aperture 130. Intima 26 is shown below first aperture 130 in FIG. 15.

Figure 16:
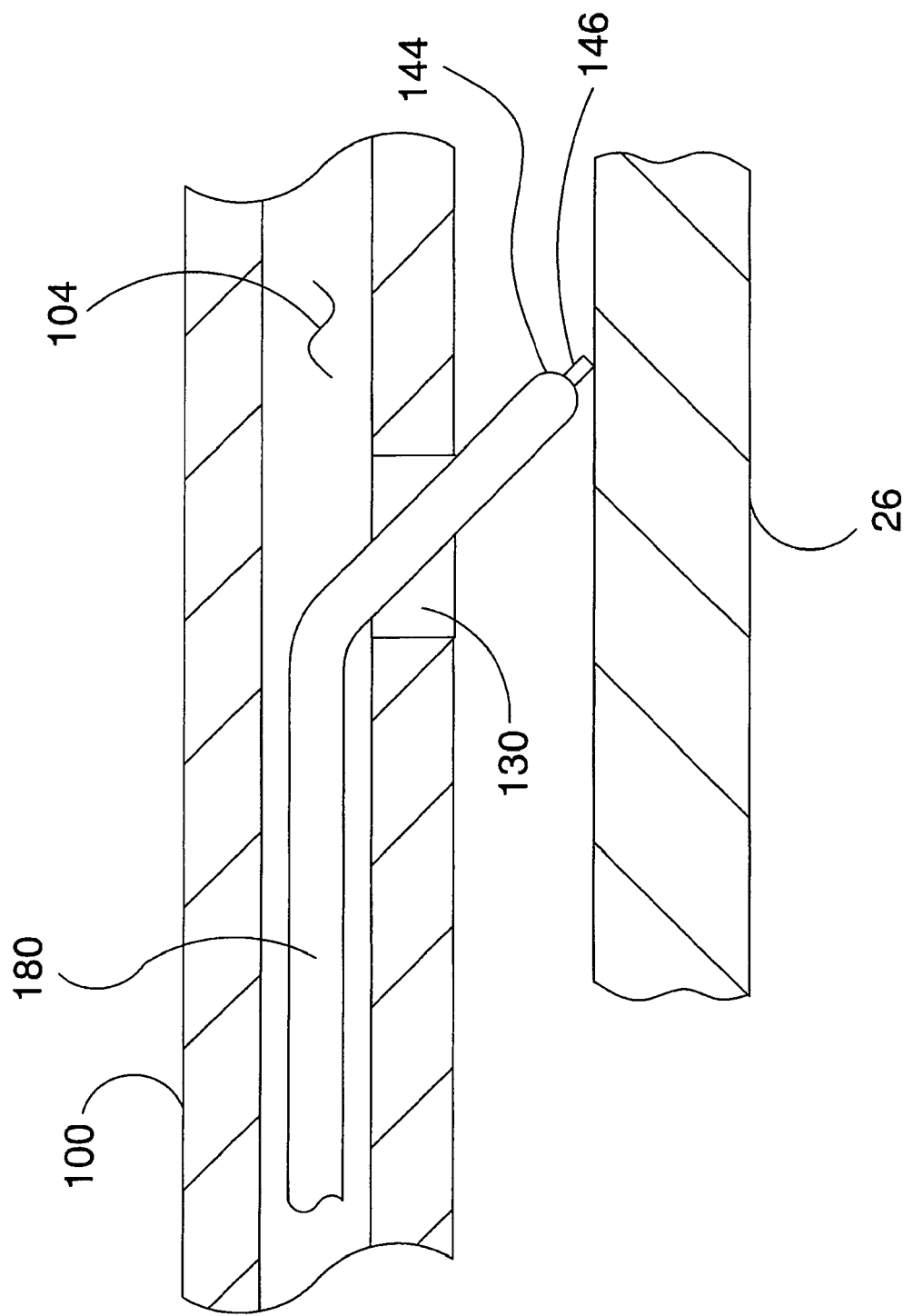
FIG. 16 is an enlarged partial cross-sectional view showing a portion of a re-entry device and the intima of a blood vessel. In the embodiment of FIG. 16, a probe of the re-entry device is contacting the intima.

FIG. 16 is an enlarged partial cross-sectional view showing a portion of re-entry device 180 and intima 26. In FIG. 16, re-entry device 180 is shown extending through central lumen 104 and first aperture 130. With reference to FIG. 16, it will be appreciated that re-entry device 180 comprises a distal surface 144 and a probe 146 extending beyond distal surface 144. In the embodiment of FIG. 16, probe 146 of re-entry device 180 is contacting intima 26.

Figure 17:
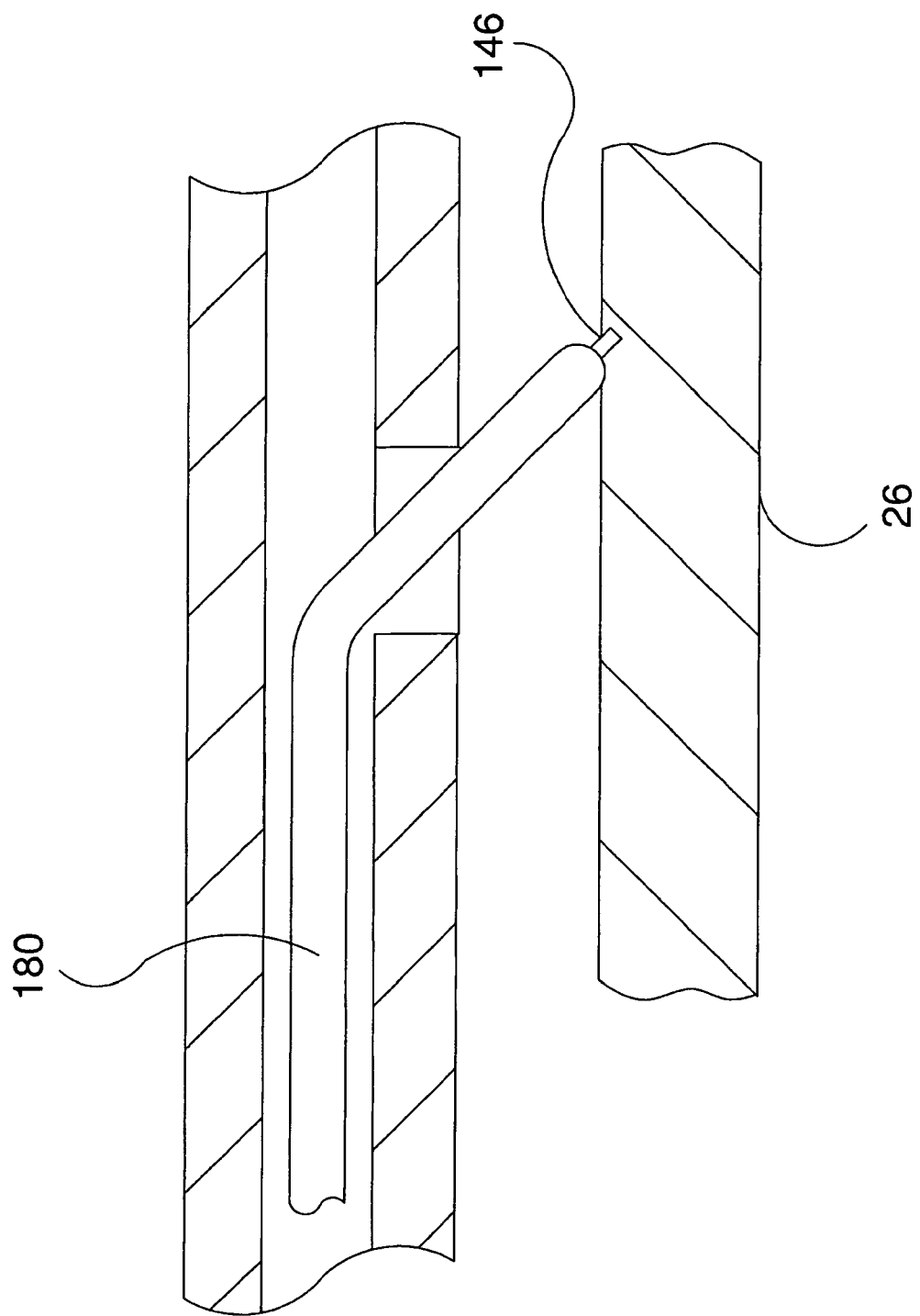
FIG. 17 is an enlarged partial cross-sectional view showing a portion of the re-entry device shown in the previous figure. In the embodiment of FIG. 17, the probe of the re-entry device has pierced the intima of the blood vessel. When this is the case, the probe may anchor the distal tip of the re-entry device to the intima. Additionally, the piercing of the intima with the probe may serve to weaken the intima.

FIG. 17 is an enlarged partial cross-sectional view showing a portion of re-entry device 180. In the embodiment of FIG. 17, probe 146 of re-entry device 180 has pierced intima 26. When this is the case, probe 146 may anchor the distal tip of re-entry device 180 to intima 26. Additionally, the piercing of intima 26 with probe 146 may serve to weaken intima 26.

Figure 18:
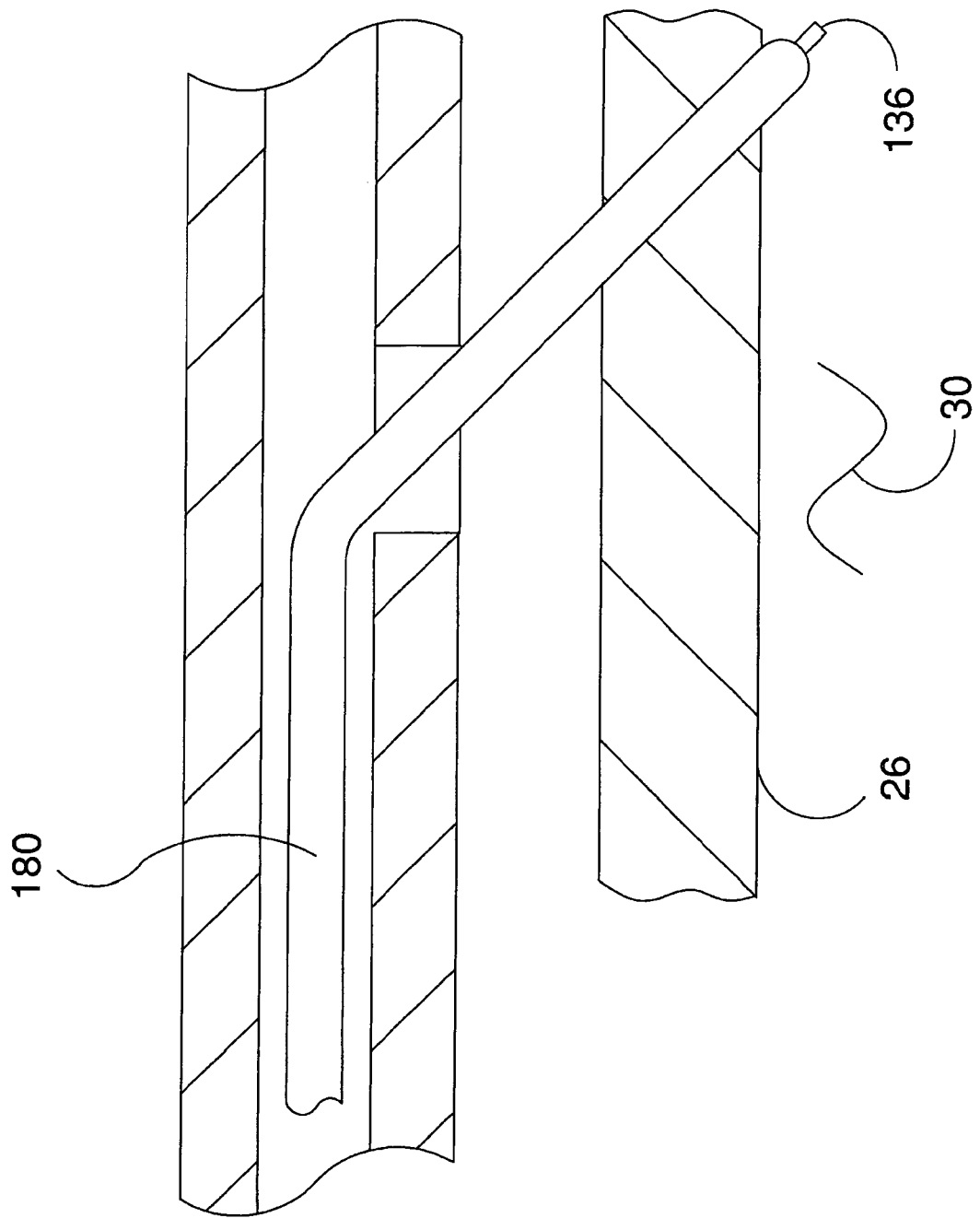
FIG. 18 is an enlarged partial cross-sectional view showing a portion of the re-entry device shown in the previous figure. In the embodiment of FIG. 18, the distal end of the re-entry device has been advanced through the intima of a blood vessel and is disposed in the true lumen of the blood vessel.

FIG. 18 is an enlarged partial cross-sectional view showing a portion of re-entry device 180. In the embodiment of FIG. 18, the distal end 136 of re-entry device 180 has been advanced through intima 26. With reference to FIG. 18, it will be appreciated that distal end 136 of re-entry device 180 is disposed in true lumen 30 defined by intima 26.

Figure 19:
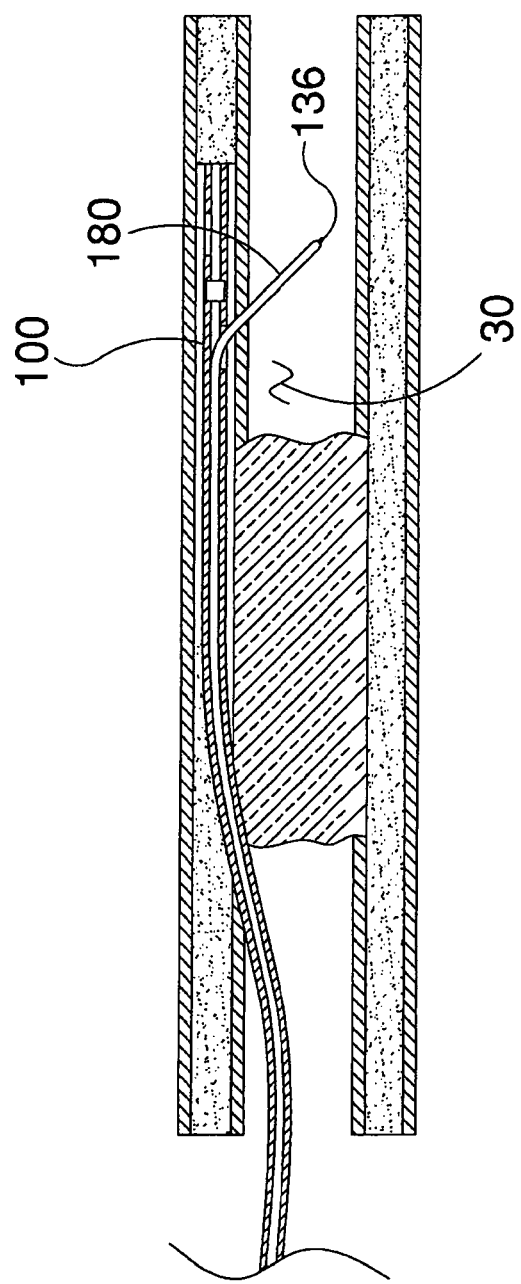
FIG. 19 is a partial cross-sectional view of the re-entry device shown in the previous figure.

FIG. 19 is a partial cross-sectional view of re-entry device 180 shown in the previous figure. FIG. 19 has a different scale than the previous figure so that more of the surrounding context is visible in FIG. 19. In FIG. 19, distal end 136 of re-entry device 180 can be seen residing in true lumen 30.

Figure 20:
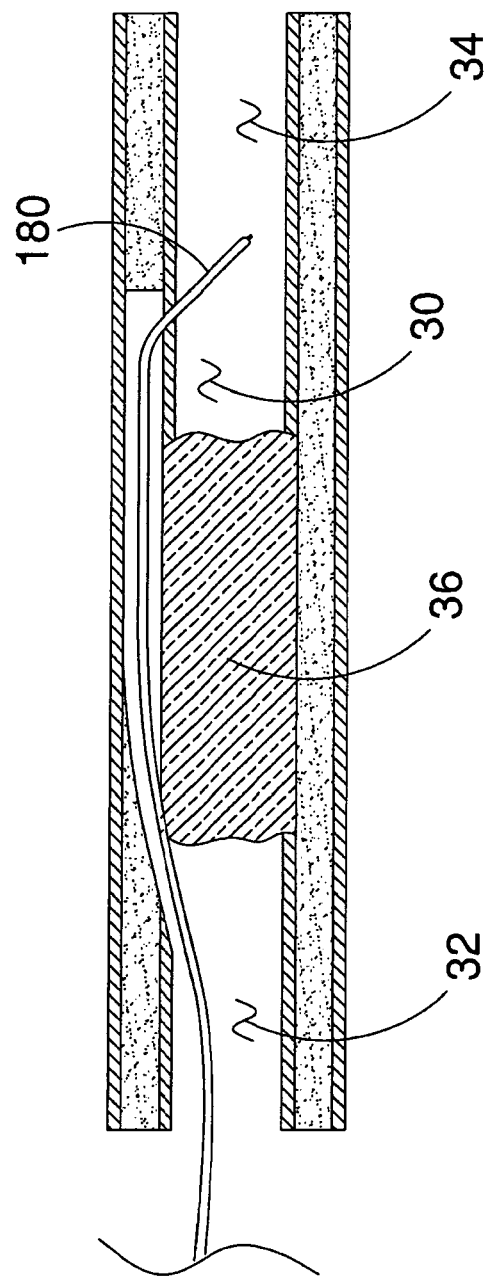
FIG. 20 is an additional view of the blood vessel shown in the previous figure. In the embodiment of FIG. 20, the orienting device has been withdrawn leaving the re-entry device in the position shown in FIG. 20. Devices such as balloon angioplasty catheters, atherectomy catheters, and stent delivery catheters may be advanced over the re-entry device. In this way, these devices may be used in conjunction with the re-entry device to establish a blood flow path between around an occlusion in a blood vessel.

FIG. 20 is an additional view of artery 20 shown in the previous figure. In the embodiment of FIG. 20, orienting device 100 has been withdrawn leaving re-entry device 180 in the position shown in FIG. 20. Devices such as balloon angioplasty catheters, atherectomy catheters, and stent delivery catheters may be advanced over re-entry device 180. In this way, these devices may be used in conjunction with re-entry device 180 to establish a blood flow path between proximal segment 32 of true lumen 30 and distal segment 34 of true lumen 30. This path allows blood to flow around occlusion 36.

Figure 21:
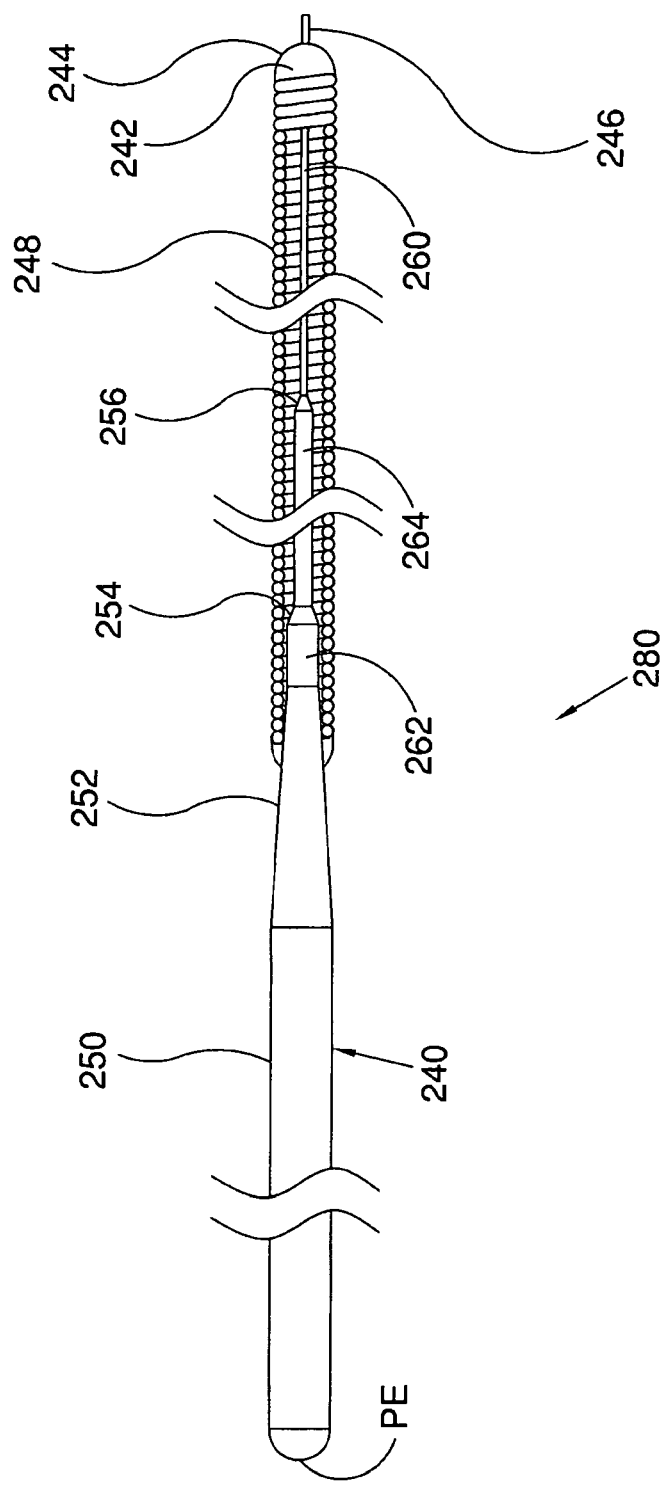
FIG. 21 is a partial cross-sectional view of an exemplary re-entry device.

FIG. 21 is a partial cross-sectional view of an exemplary re-entry device 280 in accordance with the present detailed description. Re-entry device 280 comprises a tip member 242 that is fixed to a shaft 240 and a coil 248 that is disposed about a distal portion of the shaft 240. Shaft 240 comprises a proximal segment 250 that extends between a proximal end PE and a first tapered segment 252. In the embodiment of FIG. 21, coil 248 extends between first tapered segment 252 and tip member 242.

A first intermediate segment 262 of shaft 240 extends between first tapered segment 252 and a second tapered segment 254. A second intermediate segment 264 of shaft 240 extends between second tapered segment 254 and a third tapered segment 256. A distal segment 260 of shaft 240 extends between third tapered segment 256 and tip member 242. With reference to FIG. 21, it will be appreciated that tip member 242 is fixed to distal segment 260 of shaft 240. In the embodiment of FIG. 21, a probe 246 of re-entry device 280 extends distally beyond a distal surface 244 of tip member 242.

Figure 22:
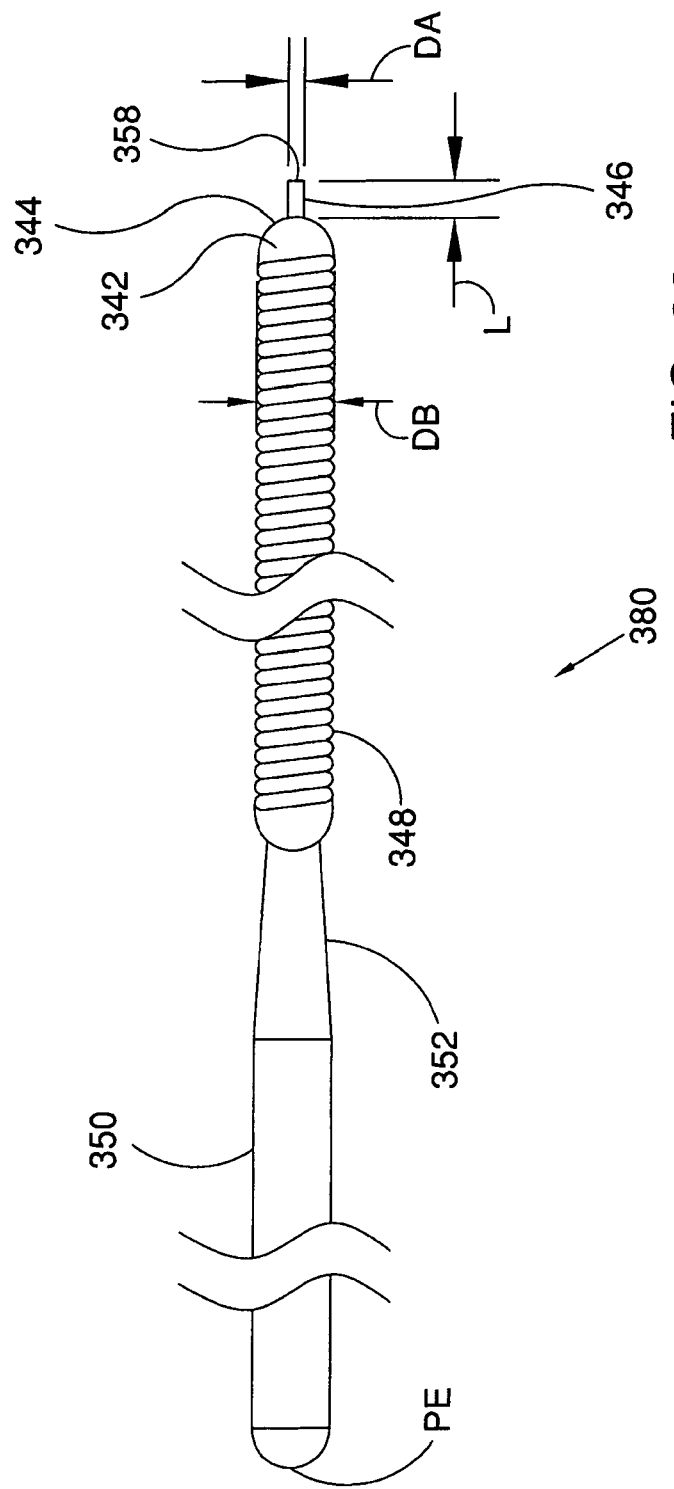
FIG. 22 is a plan view of an exemplary re-entry device.

FIG. 22 is a plan view of an exemplary re-entry device 380 in accordance with the present detailed description. Re-entry device 380 comprises a tip member 342 having a distal surface 344. In the embodiment of FIG. 22, distal surface 344 of tip member has a generally convex shape. In some cases, tip member 342 may have a generally hemispherical shape. A probe 346 of re-entry device 380 extends distally beyond distal surface 344. Probe 346 terminates at a distal face 358. In FIG. 22, distal face 358 is shown as a straight line representing a substantially flat surface. With reference to FIG. 22, it will be appreciated that distal face 358 is substantially perpendicular to the longitudinal axis of probe 346.

A number of exemplary dimensions associated with probe 346 are illustrated in FIG. 22. In the embodiment of FIG. 22, probe 346 extends beyond distal surface 344 of tip member 342 by a distance L. Also in the embodiment of FIG. 22, probe 346 has a diameter DA and tip member 342 has a diameter DB. With reference to FIG. 22, it will be appreciated that diameter DB of tip member 342 is generally greater than diameter DA of probe 346.

In some useful embodiments, diameter DA of probe 346 is between about 0.0020 inches and about 0.0055 inches. In some useful embodiments, diameter DB of tip member 342 is between about 0.008 inches and about 0.035 inches. In some useful embodiments, length L of probe 346 is between about 0.003 inches and about 0.032 inches. In FIG. 22, a coil 348 is shown extending between tip member 342 and a first tapered segment 352. Shaft 340 comprises a proximal segment 350 that extends between a proximal end PE and a first tapered segment 352.

Figure 23:
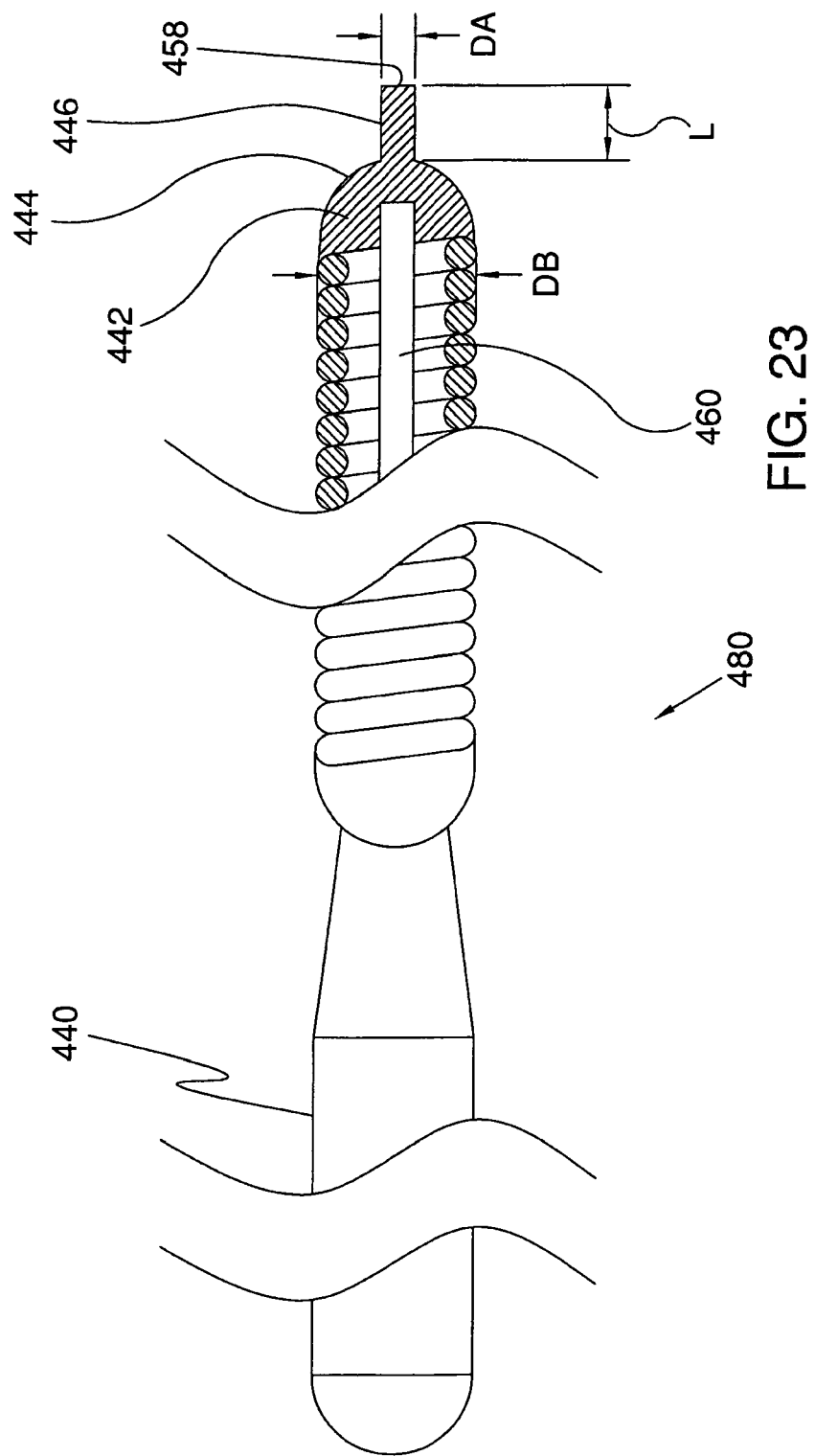
FIG. 23 is a partial cross-sectional view of an exemplary re-entry device.

FIG. 23 is a partial cross-sectional view of an exemplary re-entry device 480 in accordance with the present detailed description. Re-entry device 480 comprises a tip member 442 that is fixed to a distal segment 460 of a shaft 440. In the embodiment of FIG. 23, tip member 442 comprises a distal surface 444 and a probe 446 extending distally beyond distal surface 444. In the embodiment of FIG. 23, distal surface 444 of tip member has a generally hemispherical shape and probe 446 has a generally cylindrical shape terminating at a flat distal face 458. With reference to FIG. 23, it will be appreciated that distal face 458 is substantially perpendicular to the longitudinal axis of probe 446.

Various processes may be used to fabricate a tip member having a shape similar to tip member 442 shown in FIG. 23. A tip member may be formed, for example, using various manufacturing processes such as, for example, casting and molding. A tip member may also be fabricated by a manufacturing process comprising removing material from a piece of stock material to produce a desired profile. Examples of processes that may be used to remove material from a piece of stock material include grinding and machining (e.g., turning on a lathe).

In the embodiment of FIG. 23, probe 446 extends beyond distal surface 444 of tip member 442 by a distance L. Also in the embodiment of FIG. 23, probe 446 has a diameter DA and tip member 442 has a diameter DB. In some useful embodiments, the these dimensions fall with the numerical ranges mentioned in the detailed description of FIG. 22.

Figure 24:
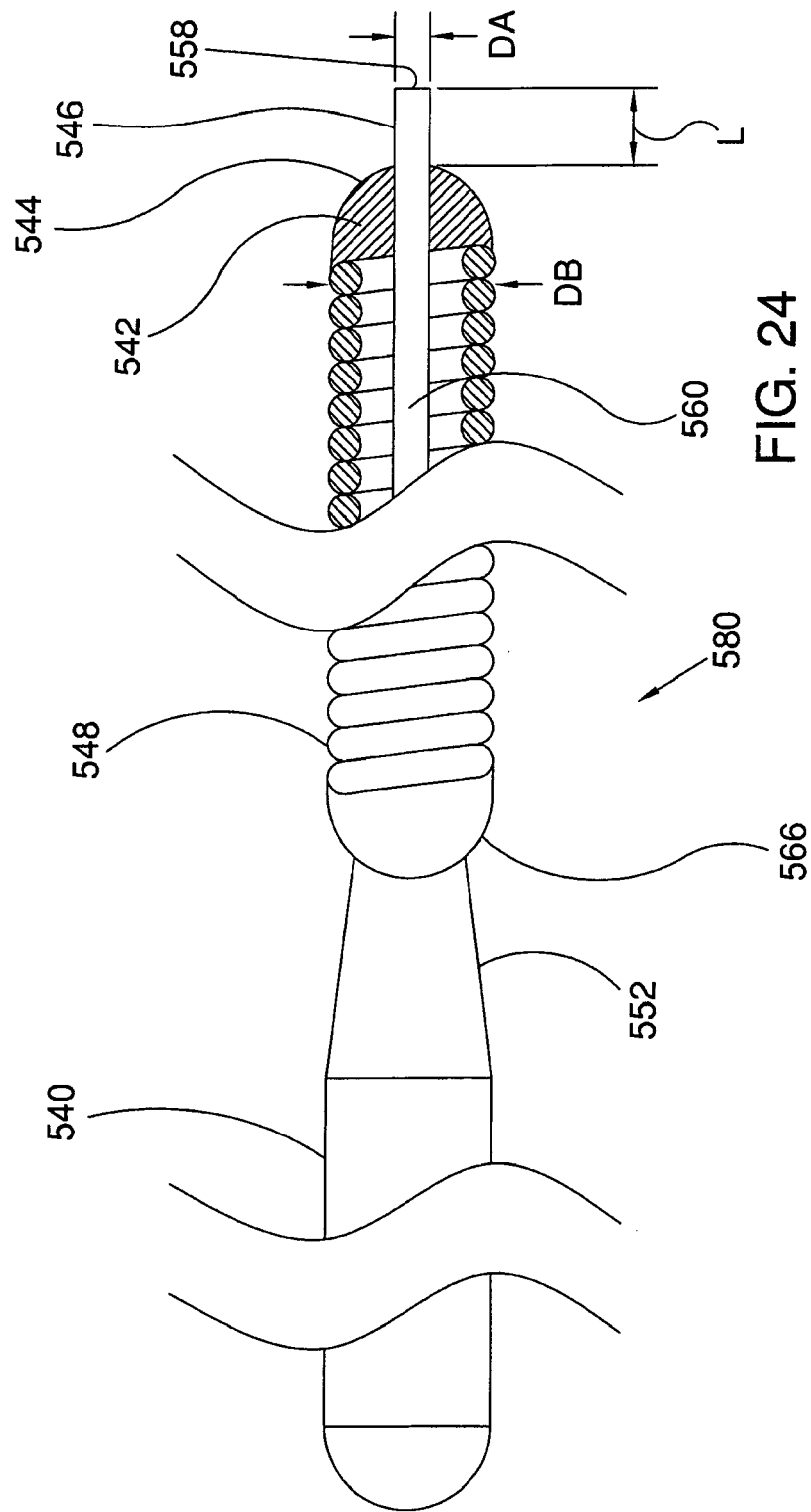
FIG. 24 is a partial cross-sectional view of an exemplary re-entry device.

FIG. 24 is a partial cross-sectional view of an exemplary re-entry device 580 in accordance with the present detailed description. Re-entry device 580 comprises a shaft 540 and a tip member 542 that is fixed to a distal segment 560 of shaft 540. A probe 546 of re-entry device 580 extends distally beyond a distal surface 544 of tip member 542. In the embodiment of FIG. 24, probe 546 comprises a portion of distal segment 560 that extends beyond distal surface 544. A coil 548 of re-entry device 580 extends between tip member 542 and a first tapered segment 552 of shaft 540. Coil 548 is fixed to first tapered section 552 at a joint 566. Joint 566 and tip member 542 may comprise, for example, silver (e.g., silver solder and/or silver braze). Joint 566 and tip member 542 may be formed using various manufacturing processes (e.g., soldering, brazing, and welding).

In the embodiment of FIG. 24, distal segment 560 of shaft 540 terminates at a substantially flat distal face 558. Probe 546 comprises a portion of distal segment 560 that extends beyond distal surface 544 of tip member 542 by a distance L. Also in the embodiment of FIG. 24, probe 546 has a diameter DA and tip member 542 has a diameter DB. In some useful embodiments, the these dimensions fall with the numerical ranges mentioned in the detailed description of FIG. 22.

Figure 25:
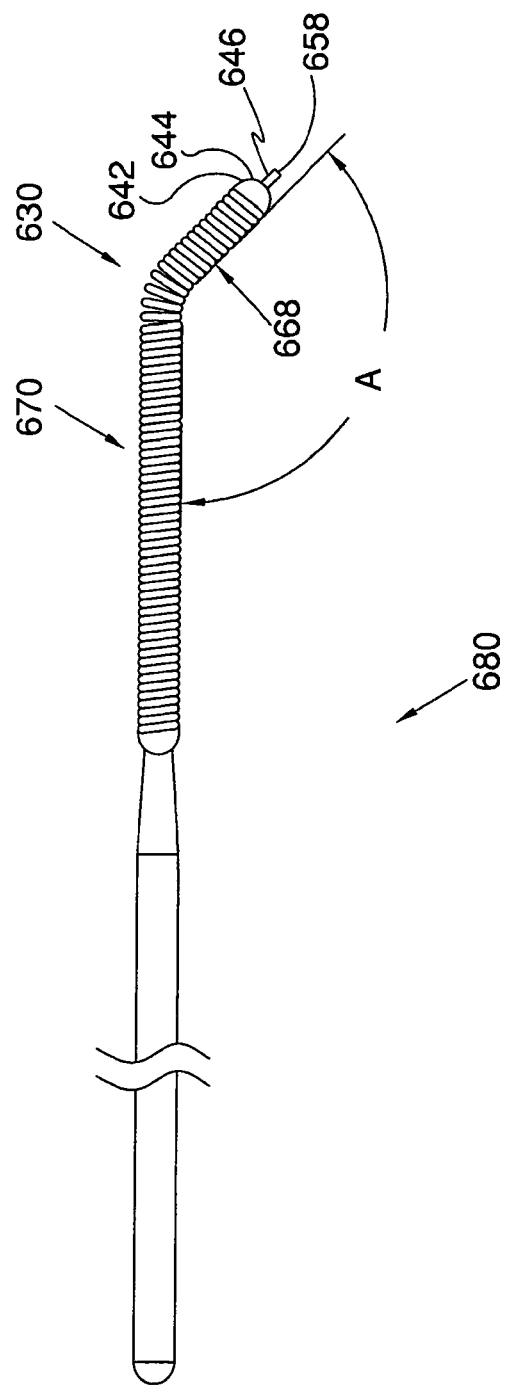
FIG. 25 is a plan view of an exemplary re-entry device.

FIG. 25 is a plan view of an exemplary re-entry device 680 in accordance with the present detailed description. Re-entry device 680 comprises a tip member 642 having a distal surface 644. In the embodiment of FIG. 25, distal surface 644 of tip member has a generally convex shape. In some cases, tip member 642 may have a generally hemispherical shape. A probe 646 of re-entry device 680 extends distally beyond distal surface 644. Probe 646 terminates at a distal face 658. In FIG. 25, distal face 658 is shown as a straight line representing a substantially flat surface.

In FIG. 25, re-entry device 600 is shown being bent at an angle A. Accordingly, it can be said that re-entry device 600 includes a bend 630. In some useful embodiments of re-entry device 600, angle A is between about 90 degrees and about 180 degrees. In some particularly useful embodiments of re-entry device 600, angle A is between about 120 degrees and about 150 degrees. Re-entry device 680 has a distal leg 668 disposed distally of bend 634 and a proximal leg 670 disposed proximally of bend 634.

Figure 26:
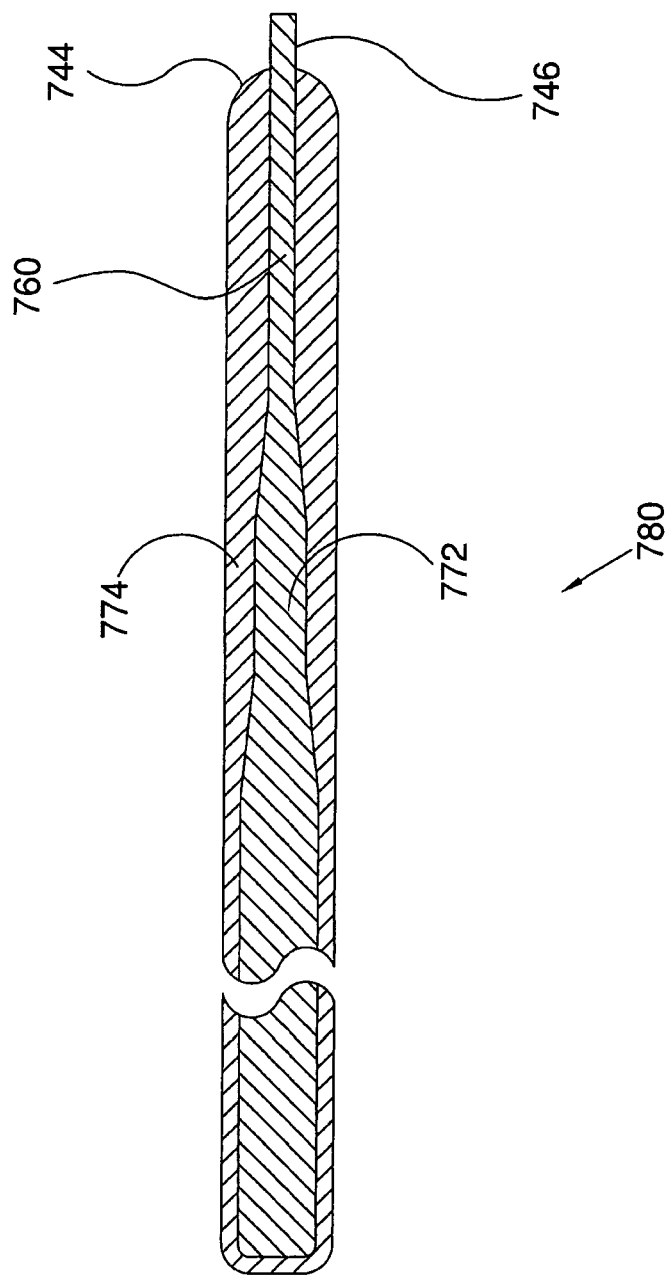
FIG. 26 is a cross-sectional view of an exemplary re-entry device.

FIG. 26 is a cross-sectional view of an exemplary re-entry device 780 in accordance with the present detailed description. Re-entry device 780 comprises a core wire 772 and a jacket 774 that is disposed about a portion of core wire 772. Jacket 774 terminates at a distal surface 744. A probe 746 of re-entry device 780 extends distally beyond distal surface 744. In the embodiment of FIG. 26, probe 746 comprises a distal segment 760 of core wire 772.

Figure 27:
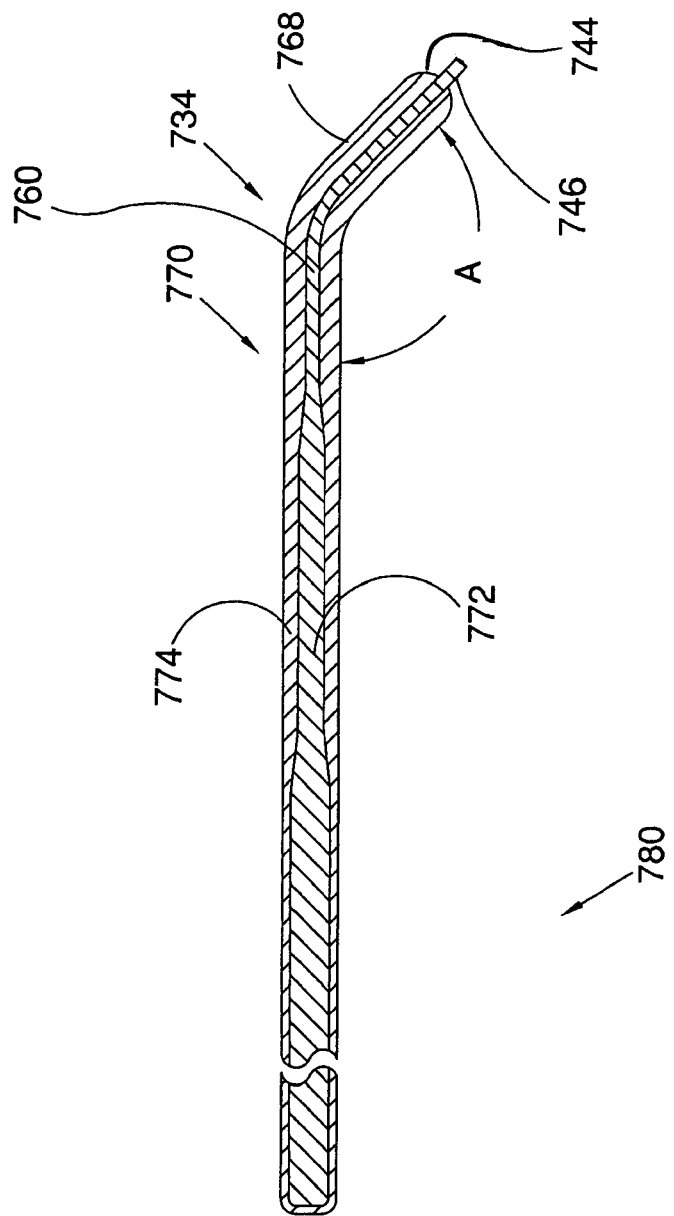
FIG. 27 is a cross-sectional view of an exemplary re-entry device.

FIG. 27 is a cross-sectional view of an exemplary re-entry device 780 in accordance with the present detailed description. Re-entry device 780 comprises a core wire 772 and a jacket 774 that is disposed about a portion of core wire 772. With reference to FIG. 27, it will be appreciated that re-entry device 780 includes a bend 734 near its distal end. Re-entry device 780 has a distal leg 768 disposed distally of bend 734 and a proximal leg 770 disposed proximally of bend 734. Distal leg 768 and proximal leg 770 define an angle A. In some useful embodiments of re-entry device 700, angle A is between about 90 degrees and about 180 degrees. In some particularly useful embodiments of re-entry device 700, angle A is between about 120 degrees and about 150 degrees. Jacket 774 of re-entry device 780 terminates at a distal surface 744. A probe 746 of re-entry device 780 extends distally beyond distal surface 744. In the embodiment of FIG. 27, probe 746 comprises a distal segment 760 of core wire 772.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed:

1. An elongate medical device for penetrating tissue, comprising:
    an elongate shaft having a proximal segment and a reduced diameter distal segment, the distal segment unitarily formed with the proximal segment;
    a coil positioned around the distal segment;
    a tip member fixedly securing a distal end of the coil to the distal segment; and
    a distal portion of the distal segment extending distal of the distal end of the coil and extending distal of a distalmost end of the tip member;
    wherein the distal portion of the distal segment defines a probe adapted and configured to pierce tissue.

2. The elongate medical device of claim 1, wherein the probe defines a distalmost end of the elongate medical device.

3. The elongate medical device of claim 1, wherein the probe is exposed from all other components of the elongate medical device.

4. The elongate medical device of claim 1, wherein the elongate shaft includes a tapered segment between the proximal segment and the distal segment.

5. The elongate medical device of claim 4, wherein a proximal end of the coil is secured to the tapered segment of the elongate shaft.

6. The elongate medical device of claim 5, wherein the proximal segment has a constant diameter.

7. The elongate medical device of claim 6, wherein the distal segment has a constant diameter.

8. The elongate medical device of claim 1, wherein the probe extends distally beyond all other components of the elongate medical device by a distance that is greater than 0.003 inches.

9. The elongate medical device of claim 8, wherein the probe extends distally beyond all other components of the elongate medical device by a distance that is less than 0.012 inches.

10. The elongate medical device of claim 1, wherein the elongate shaft comprises a bend disposed between the proximal segment and the distal portion of the distal segment such that the distal portion of the distal segment extends at an angle to the proximal segment, the angle being greater than 90 degrees and less than 180 degrees.

11. The elongate medical device of claim 10, wherein the angle is greater than 120 degrees and less than 150 degrees.

12. An elongate medical device for penetrating tissue, comprising:
    an elongate shaft having a proximal segment and a reduced diameter distal segment, the distal segment unitarily formed with the proximal segment;
    a tubular component positioned around and fixedly secured to the distal segment of the elongate shaft; and
    a distal portion of the distal segment extending distal of a distal end of the tubular component and forming a probe adapted and configured to pierce tissue;
    the probe being exposed from all other components of the elongate medical device and defining a distalmost end of the elongate medical device.

13. The elongate medical device of claim 12, wherein the elongate shaft includes a tapered segment between the proximal segment and the distal segment.

14. The elongate medical device of claim 13, wherein a proximal end of the tubular component is secured to the tapered segment of the elongate shaft.

15. The elongate medical device of claim 14, wherein the proximal segment has a constant diameter.

16. The elongate medical device of claim 15, wherein the distal segment has a constant diameter.

17. The elongate medical device of claim 12, wherein the probe extends distally beyond all other components of the elongate medical device by a distance that is greater than 0.003 inches.

18. The elongate medical device of claim 17, wherein the probe extends distally beyond all other components of the elongate medical device by a distance that is less than 0.012 inches.

19. The elongate medical device of claim 12, wherein the elongate shaft comprises a bend disposed between the proximal segment and the distal portion of the distal segment such that the distal portion of the distal segment extends at an angle to the proximal segment, the angle being greater than 90 degrees and less than 180 degrees.

20. The elongate medical device of claim 19, wherein the angle is greater than 120 degrees and less than 150 degrees.

* * * * *